United States Patent
Kane

(10) Patent No.: US 7,983,932 B2
(45) Date of Patent: Jul. 19, 2011

(54) NETWORK AND METHODS FOR INTEGRATING INDIVIDUALIZED CLINICAL TEST RESULTS AND NUTRITIONAL TREATMENT

(75) Inventor: Edward Kane, Millville, NJ (US)

(73) Assignee: Bodybio, Inc, Millville, NJ (US)

( * ) Notice: Subject to any disclaimer, the term of this patent is extended or adjusted under 35 U.S.C. 154(b) by 1396 days.

(21) Appl. No.: 11/058,174

(22) Filed: Feb. 16, 2005

(65) Prior Publication Data

US 2005/0177397 A1   Aug. 11, 2005

Related U.S. Application Data

(60) Provisional application No. 60/545,677, filed on Feb. 17, 2004.

(51) Int. Cl.
  *G06Q 10/00* (2006.01)
  *G06Q 50/00* (2006.01)
(52) U.S. Cl. .......................................................... 705/2
(58) Field of Classification Search .................. 705/2, 4, 705/9; 600/300; 128/630
  See application file for complete search history.

(56) References Cited

U.S. PATENT DOCUMENTS

| | | | |
|---|---|---|---|
| 4,531,527 A | 7/1985 | Reinhold et al. | |
| 4,712,562 A | 12/1987 | Ohayon et al. | |
| 4,838,275 A | 6/1989 | Lee et al. | |
| 5,012,411 A | 4/1991 | Policastro et al. | |
| 5,746,204 A * | 5/1998 | Schauss | 600/300 |
| 5,950,640 A * | 9/1999 | Duncan et al. | 132/305 |
| 6,063,026 A * | 5/2000 | Schauss et al. | 600/300 |
| 6,234,964 B1 * | 5/2001 | Iliff | 600/300 |
| 6,277,070 B1 * | 8/2001 | Kane et al. | 600/300 |
| 2003/0009367 A1 * | 1/2003 | Morrison | 705/9 |
| 2003/0110059 A1 * | 6/2003 | Janas et al. | 705/2 |

OTHER PUBLICATIONS

International Search Report.

* cited by examiner

*Primary Examiner* — Gerald J. O'Connor
*Assistant Examiner* — John A Pauls

(57) ABSTRACT

The present invention provides networks and method for linking consumers and nutritional pharmacologists offering personalized nutritional information through a central network site. The network includes a central integration site through which network members communicate with each other. The central integration site stores two or more databases in the storage medium. The databases store biochemical marker data information, nutritional and/or drug data information including a record for association and effect of nutrients with a particular biochemical marker, and/or drug. The network of the invention provides individualized nutritional diagnostic and treatment to consumers on the basis of their clinical test results.

8 Claims, 20 Drawing Sheets

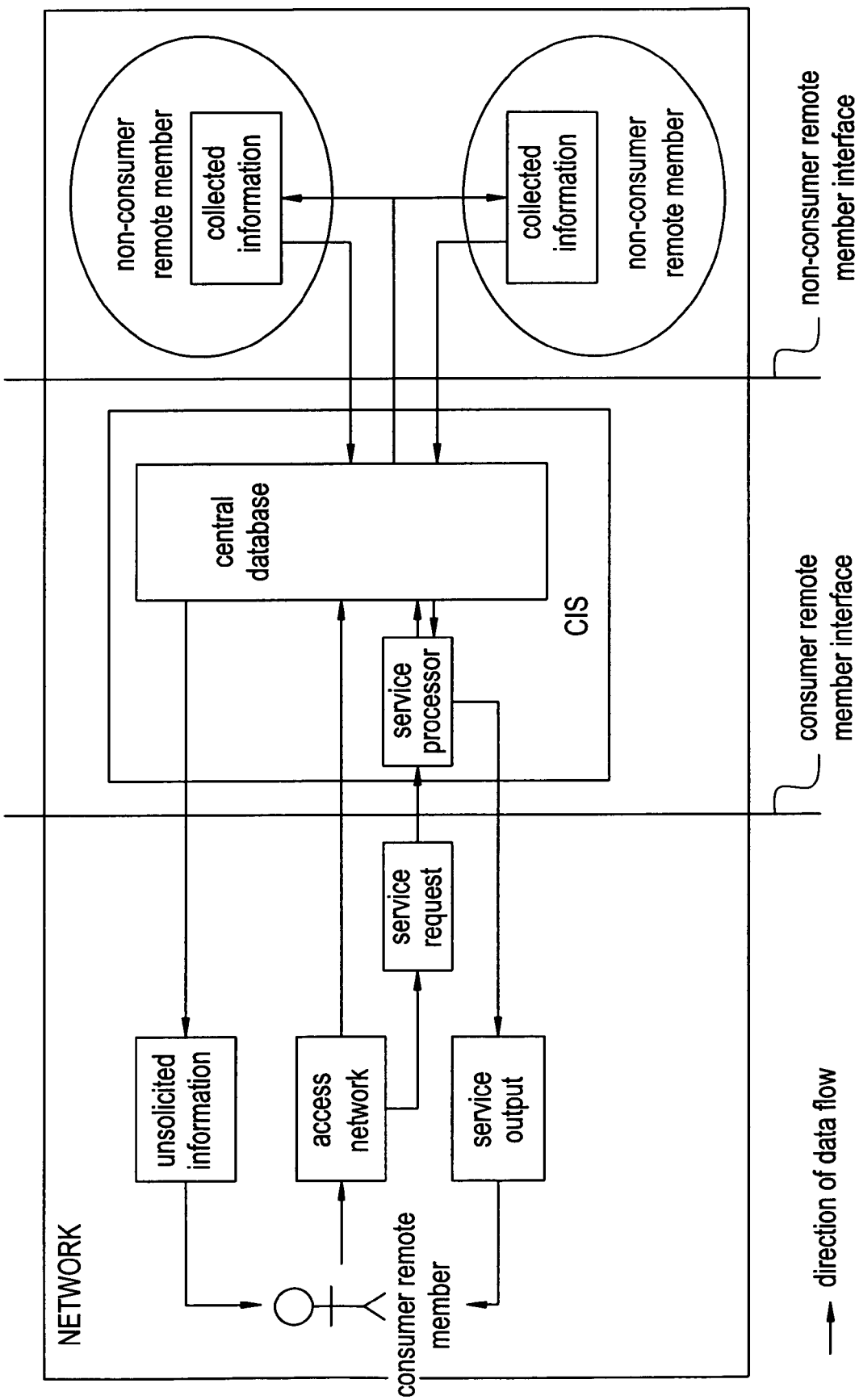

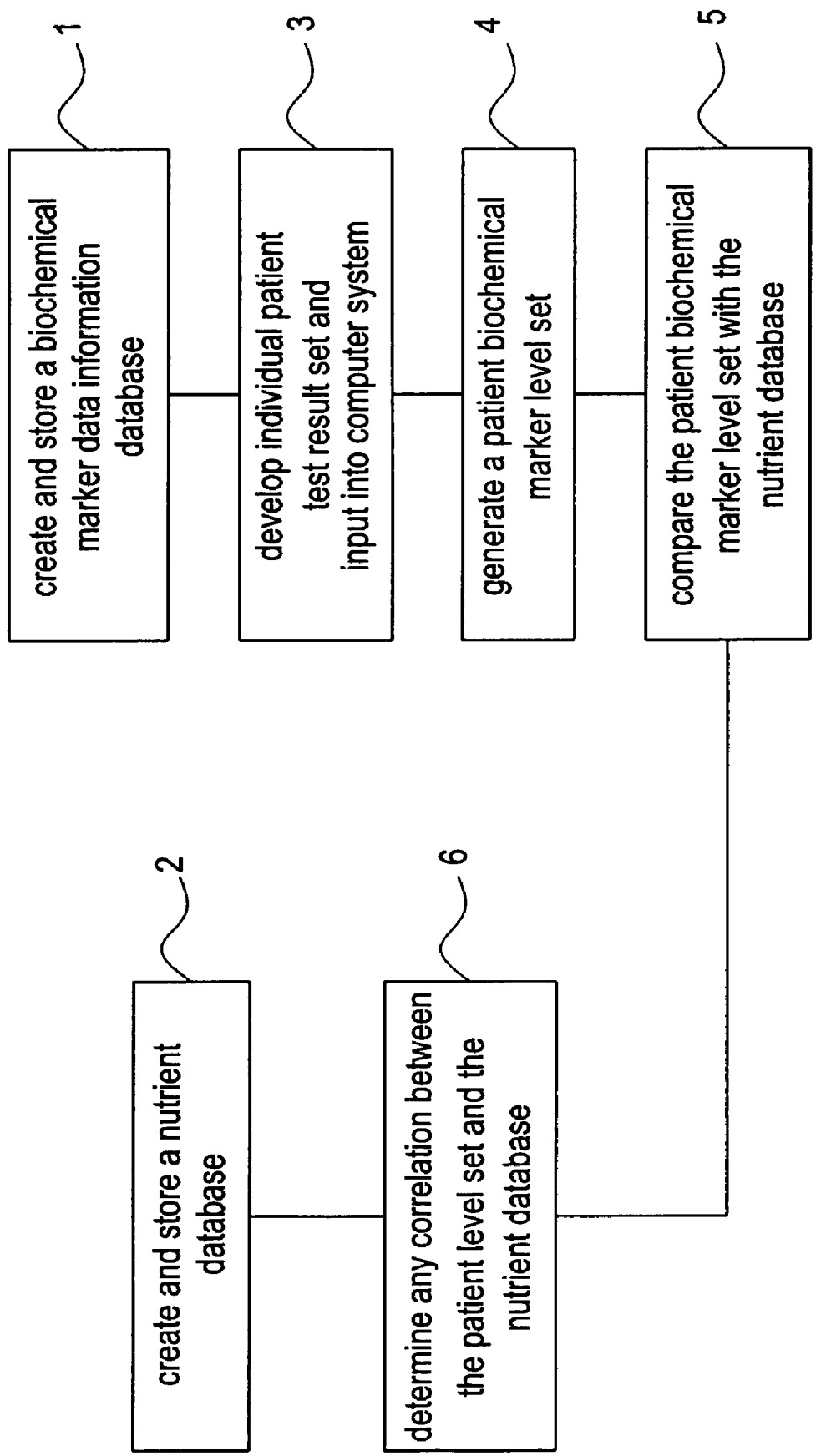

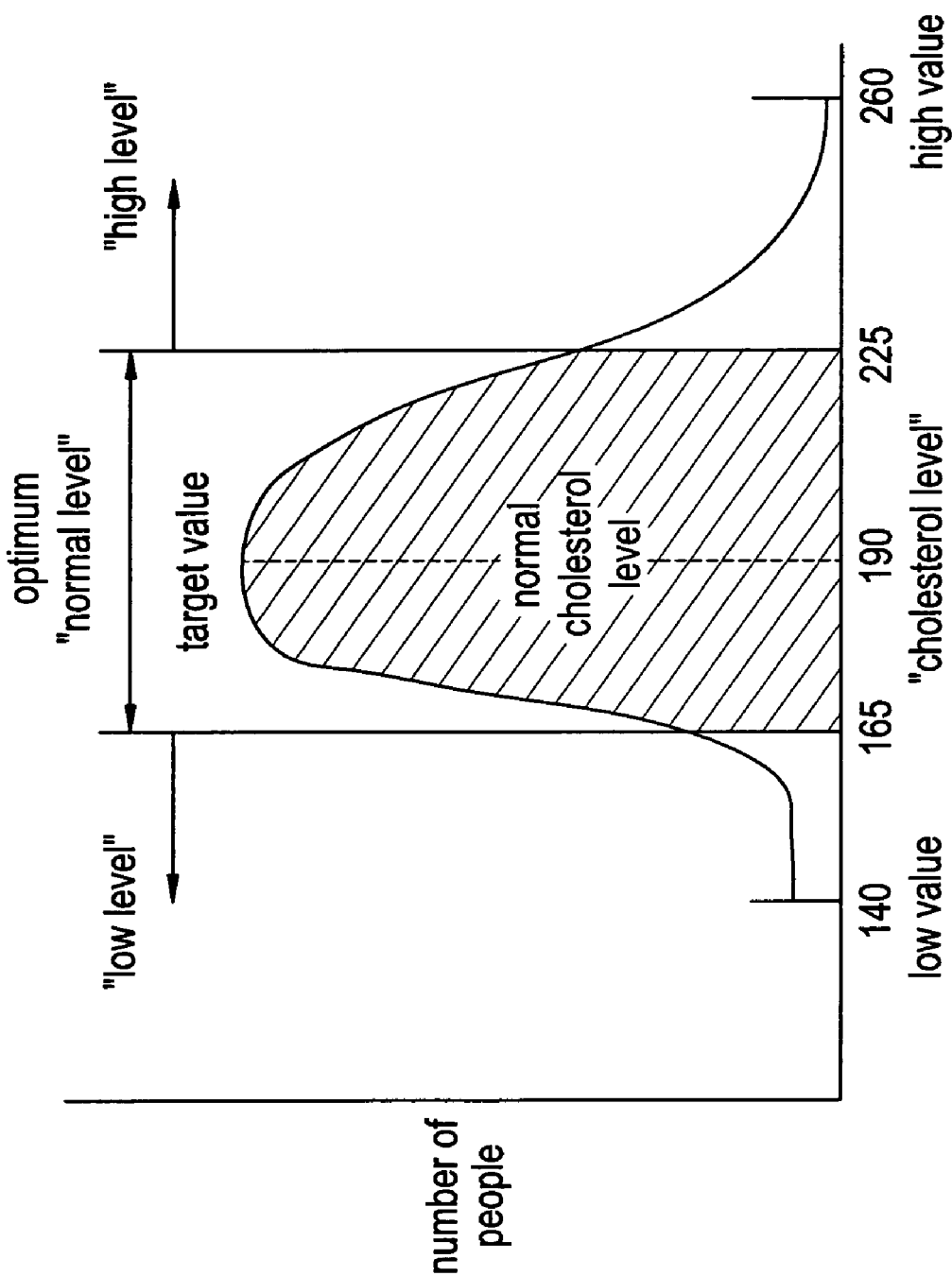

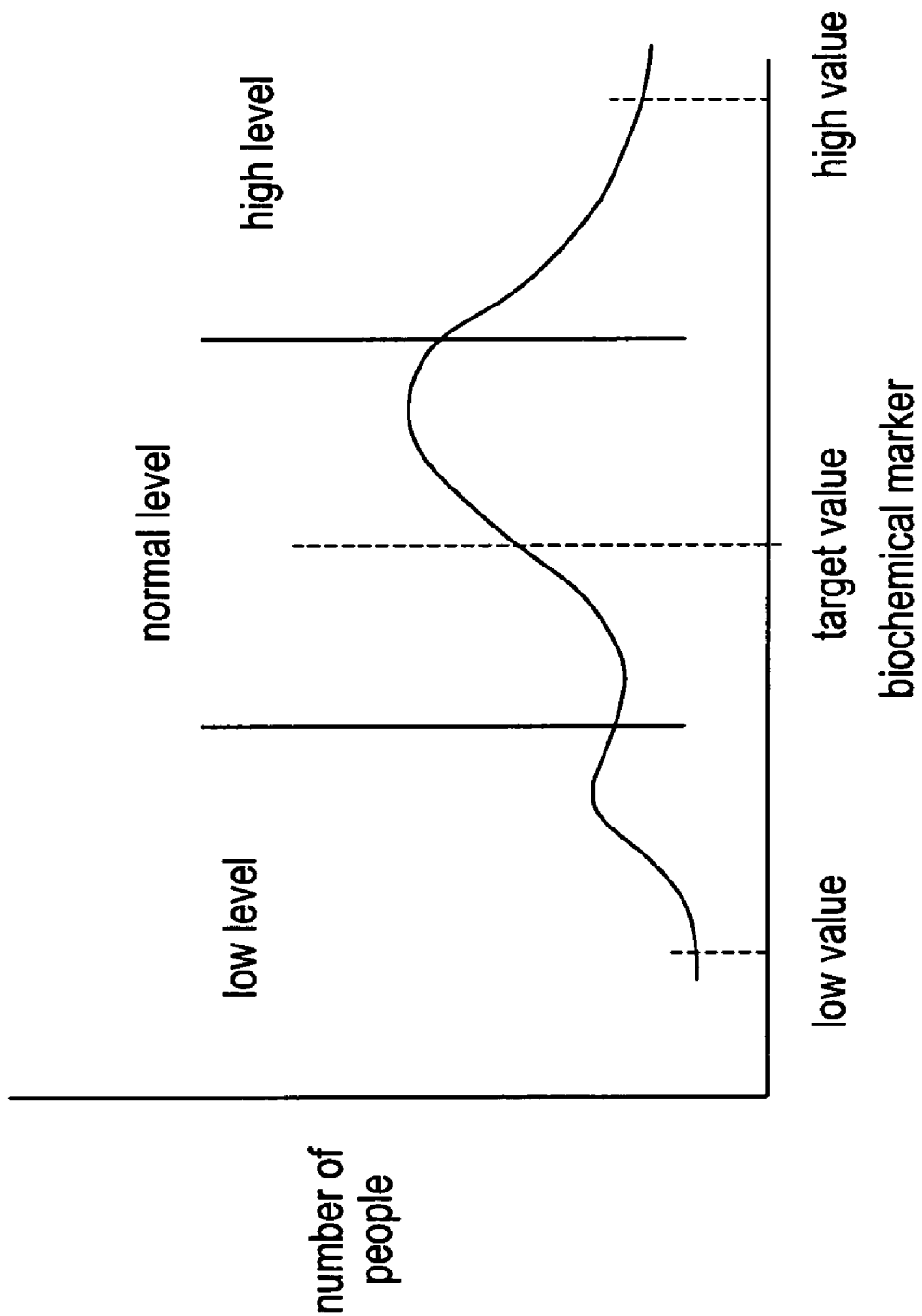

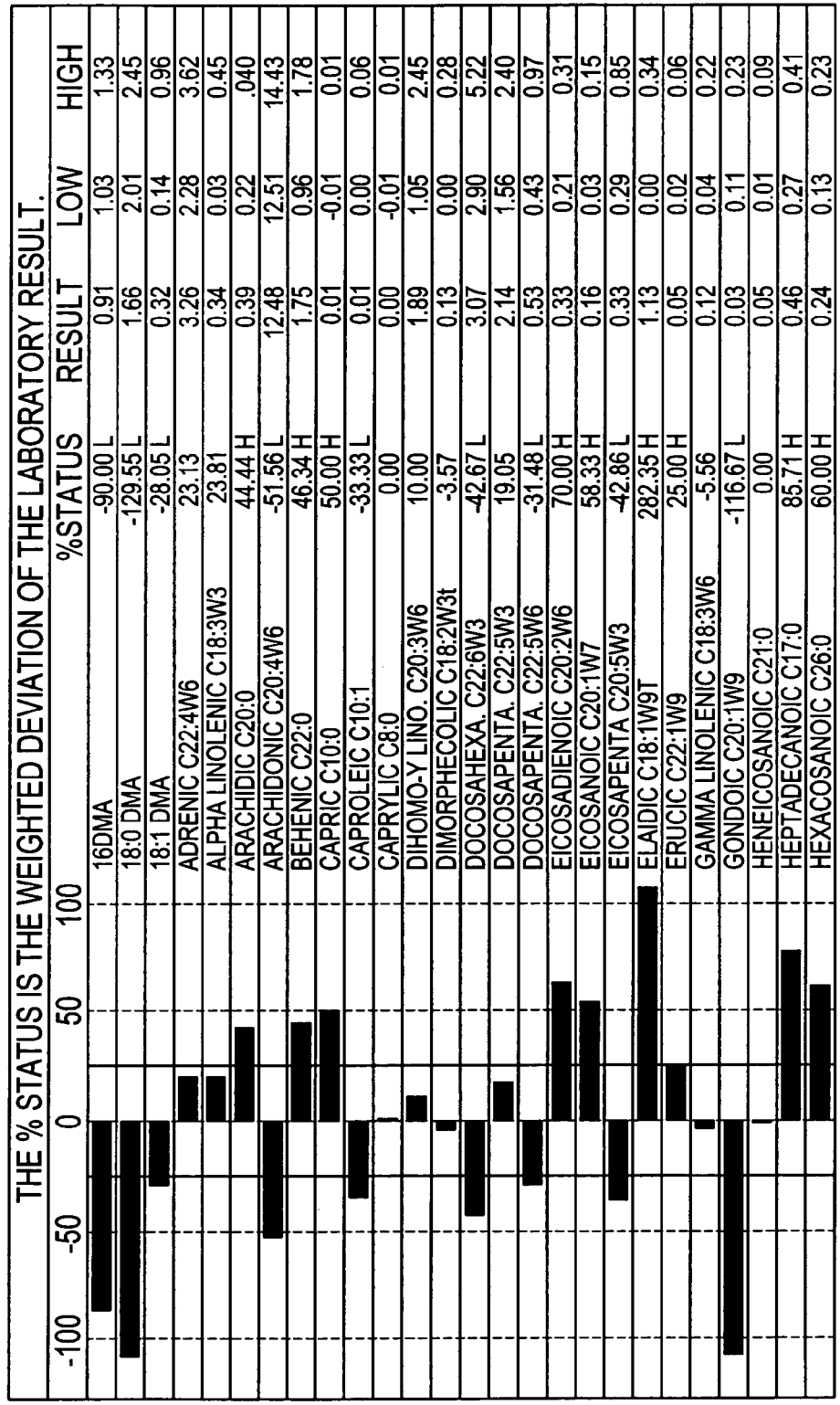

FIG. 9A-1

BASIC STATUS REPORT
FATTY ACID RED CELL MEMBRANE
PRACTITIONER:

| | %STATUS | RESULT | LOW | HIGH |
|---|---|---|---|---|
| 16DMA | -90.00 L | 0.91 | 1.03 | 1.33 |
| 18:0 DMA | -129.55 L | 1.66 | 2.01 | 2.45 |
| 18:1 DMA | -28.05 L | 0.32 | 0.14 | 0.96 |
| ADRENIC C22:4W6 | 23.13 | 3.26 | 2.28 | 3.62 |
| ALPHA LINOLENIC C18:3W3 | 23.81 | 0.34 | 0.03 | 0.45 |
| ARACHIDIC C20:0 | 44.44 H | 0.39 | 0.22 | .040 |
| ARACHIDONIC C20:4W6 | -51.56 L | 12.48 | 12.51 | 14.43 |
| BEHENIC C22:0 | 46.34 H | 1.75 | 0.96 | 1.78 |
| CAPRIC C10:0 | 50.00 H | 0.01 | -0.01 | 0.01 |
| CAPROLEIC C10:1 | -33.33 L | 0.01 | 0.00 | 0.06 |
| CAPRYLIC C8:0 | 0.00 | 0.00 | -0.01 | 0.01 |
| DIHOMO-Y LINO. C20:3W6 | 10.00 | 1.89 | 1.05 | 2.45 |
| DIMORPHECOLIC C18:2W3t | -3.57 | 0.13 | 0.00 | 0.28 |
| DOCOSAHEXA. C22:6W3 | -42.67 L | 3.07 | 2.90 | 5.22 |
| DOCOSAPENTA. C22:5W3 | 19.05 | 2.14 | 1.56 | 2.40 |
| DOCOSAPENTA. C22:5W6 | -31.48 L | 0.53 | 0.43 | 0.97 |
| EICOSADIENOIC C20:2W6 | 70.00 H | 0.33 | 0.21 | 0.31 |
| EICOSANOIC C20:1W7 | 58.33 H | 0.16 | 0.03 | 0.15 |
| EICOSAPENTA C20:5W3 | -42.86 L | 0.33 | 0.29 | 0.85 |
| ELAIDIC C18:1W9T | 282.35 H | 1.13 | 0.00 | 0.34 |
| ERUCIC C22:1W9 | 25.00 H | 0.05 | 0.02 | 0.06 |
| GAMMA LINOLENIC C18:3W6 | -5.56 | 0.12 | 0.04 | 0.22 |
| GONDOIC C20:1W9 | -116.67 L | 0.03 | 0.11 | 0.23 |
| HENEICOSANOIC C21:0 | 0.00 | 0.05 | 0.01 | 0.09 |
| HEPTADECANOIC C17:0 | 85.71 H | 0.46 | 0.27 | 0.41 |
| HEXACOSANOIC C26:0 | 60.00 H | 0.24 | 0.13 | 0.23 |

THE % STATUS IS THE WEIGHTED DEVIATION OF THE LABORATORY RESULT.

BASIC STATUS REPORT
FATTY ACID RED CELL MEMBRANE

FIG. 9C-1

BASIC STATUS REPORT

PATIENT ID:  PRACTITIONER:  BLOOD TEST DATE:

THE % STATUS IS THE WEIGHTED DEVIATION OF THE LABORATORY RESULT.

| | %STATUS | RESULT | LOW | HIGH |
|---|---|---|---|---|
| A/G RATIO | 30.00 H | 1.76 | 0.80 | 2.00 |
| ALBUMIN | -13.16 | 4.40 | 3.70 | 5.60 |
| ALKALINE PHOSPHATASE | -26.46 L | 223.00 | 130.00 | 525.00 |
| ANION GAP | 43.00 H | 19.30 | 10.00 | 20.00 |
| B.U.N. | -33.33 L | 10.00 | 8.00 | 20.00 |
| B.U.N./CREATININE RATIO | -28.95 L | 10.00 | 6.00 | 25.00 |
| BASOPHIL COUNT | -26.00 L | 48.00 | 0.00 | 200.00 |
| BASOPHILS | 0.00 | 1.00 | 0.00 | 2.00 |
| BILIRUBIN, TOTAL | -25.00 L | 0.50 | 0.20 | 1.40 |
| CALCIUM | -10.00 | 9.80 | 9.20 | 10.70 |
| CALCIUM/PHOSPHORUS RATIO | -8.48 | 2.13 | 1.30 | 3.30 |
| CHLORIDE | 25.00 H | 106.00 | 100.00 | 108.00 |
| CHOLESTEROL | -2.45 | 165.00 | 97.00 | 240.00 |
| CO2 | -83.33 L | 22.00 | 24.00 | 30.00 |
| CREATININE | 16.67 | 1.00 | 0.60 | 1.20 |
| EOSINOPHIL COUNT | -2.00 | 240.00 | 0.00 | 500.00 |
| EOSINOPHILS | 50.00 H | 5.00 | 0.00 | 5.00 |
| FREE T4 INDEX (T7) | -37.50 L | 1.40 | 1.05 | 3.85 |
| GGT | 159.52 H | 56.00 | 12.00 | 33.00 |
| GLOBULIN | -12.50 | 2.50 | 1.90 | 3.50 |
| GLUCOSE | -9.52 | 91.00 | 74.00 | 116.00 |
| HDL | -33.33 L | 40.00 | 35.00 | 65.00 |
| HEMATOCRIT | -27.42 L | 44.30 | 42.90 | 49.10 |
| HEMOGLOBIN | 0.00 | 15.50 | 14.40 | 16.60 |
| IRON, TOTAL | -22.64 | 57.00 | 28.00 | 134.00 |

FIG. 9D-1

BASIC STATUS REPORT

PATIENT ID:                           BLOOD TEST DATE:

THE % STATUS IS THE WEIGHTED DEVIATION OF THE LABORATORY RESULT.

*LOW RESULTS*

| -100 | -75 | -50 | -25 | 0 | | %STATUS | RESULT | LOW | HIGH |
|---|---|---|---|---|---|---|---|---|---|
| | | | | | CO2 | -83.33 L | 22.00 | 24.00 | 30.00 |
| | | | | | THYROXINE (T4) | -48.65 L | 5.10 | 5.00 | 12.40 |
| | | | | | W.B.C. | -46.47 L | 4.80 | 4.50 | 13.00 |
| | | | | | NEUTROPHIL COUNT | -44.97 L | 2112.00 | 1800.00 | 8000.00 |
| | | | | | NEUTROPHILS | -42.59 L | 44.00 | 42.00 | 69.00 |
| | | | | | SGPT | -41.43 L | 13.00 | 10.00 | 45.00 |
| | | | | | FREE T4 INDEX (T7) | -37.50 L | 1.40 | 1.05 | 3.85 |
| | | | | | R.B.C. | -36.84 L | 4.83 | 4.73 | 5.49 |
| | | | | | B.U.N. | -33.33 L | 10.00 | 8.00 | 20.00 |
| | | | | | HDL | -33.33 L | 40.00 | 35.00 | 65.00 |
| | | | | | SGOT | -30.00 L | 20.00 | 15.00 | 40.00 |
| | | | | | LDH | -29.41 L | 155.00 | 120.00 | 290.00 |
| | | | | | LYMPHOCYTE COUNT | -29.13 L | 2160.00 | 1200.00 | 5800.00 |
| | | | | | B.U.N./CREATININE RATIO | -28.95 L | 10.00 | 6.00 | 25.00 |
| | | | | | HEMATOCRIT | -27.42 L | 44.30 | 42.90 | 49.10 |
| | | | | | ULTRA-SENSITIVE TSH | -27.08 L | 1.40 | 0.30 | 5.10 |
| | | | | | ALKALINE PHOSPHATASE | -26.46 L | 223.00 | 130.00 | 525.00 |
| | | | | | BASOPHIL COUNT | -26.00 L | 48.00 | 0.00 | 200.00 |
| | | | | | BILIRUBIN, TOTAL | -25.00 L | 0.50 | 0.20 | 1.40 |

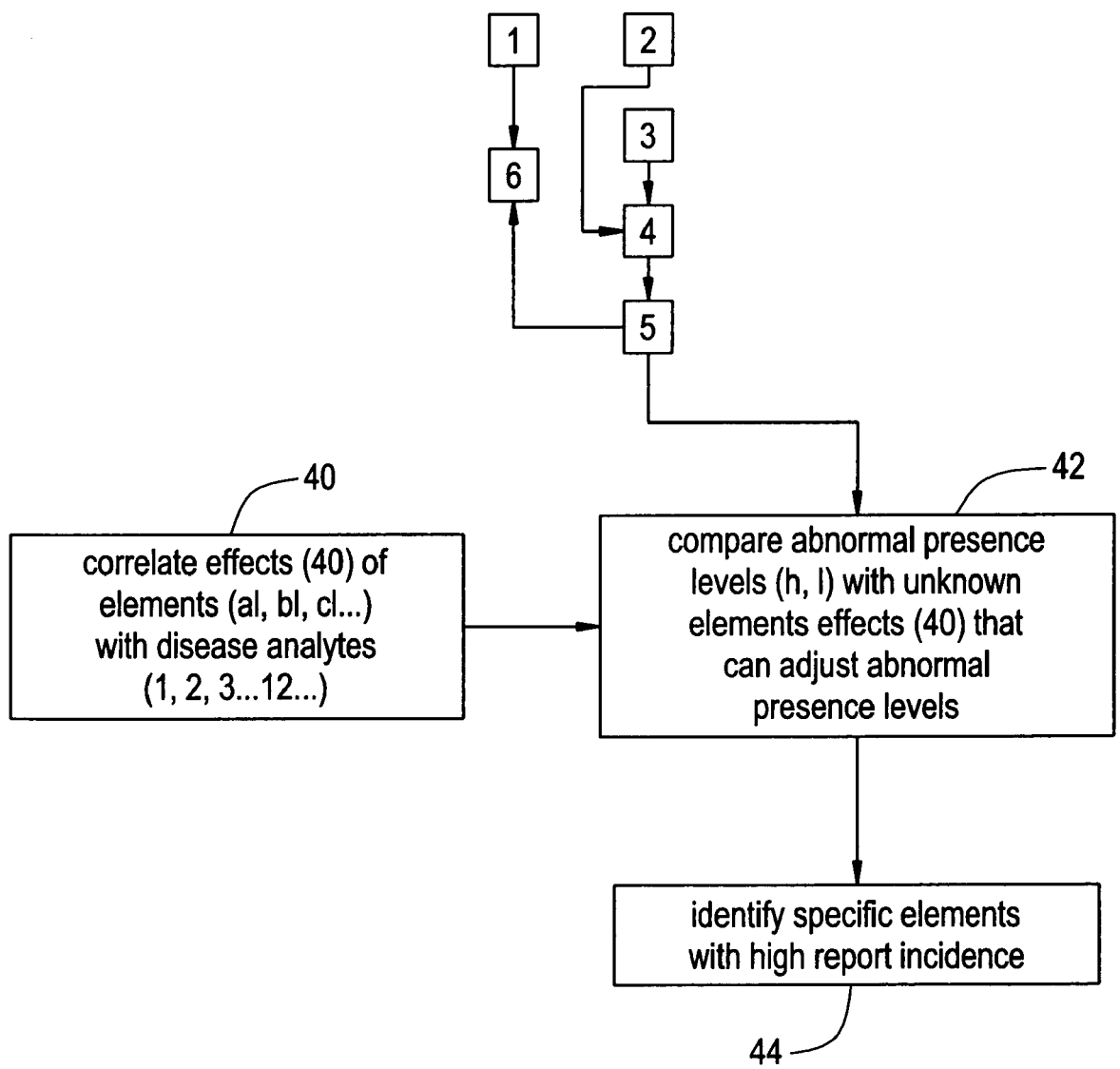

NETWORK AND METHODS FOR INTEGRATING INDIVIDUALIZED CLINICAL TEST RESULTS AND NUTRITIONAL TREATMENT

CROSS REFERENCE TO RELATED APPLICATIONS

This application claims priority under 35 U.S.C. §119 based upon U.S. Provisional Patent Application No: 60/545,677, filed Feb. 17, 2004.

I. FIELD OF THE INVENTION

The present invention relates to systems and methods for facilitating automated nutritional diagnostic and treatment. More particularly, the invention relates to an interactive network and method for generating consumer individualized status reports.

II. BACKGROUND OF THE INVENTION

The early detection and treatment of numerous diseases could keep many patients from reaching advanced stages of illness, the treatment of which is a significant part of the financial burden attributed to our nation's health care system. If the public had universal, unrestricted and easy access to medical information, many diseases could be prevented.

Health care costs currently represent 14% of the United States Gross National Product and are rising faster than any other component of the Consumer Price Index. Moreover, usually because of an inability to pay for medical services, many people are deprived of access to even the most basic medical care and information. Many people are delayed in obtaining, or are prevented from seeking, medical attention because of cost, time constraints, or inconvenience. It is obvious that the United States is facing health-related issues of enormous proportions and that present solutions are not robust.

The complexity and interrelationships of various diseases and the biochemical markers that may be associated with these diseases are sufficient to tax the capacity of most medical practitioners. To aid medical practitioners in disease diagnosis, computerized expert systems have been developed to correlate medical diagnostic data with various diseases to guide physicians in prescribing treatments for their patients.

A prior attempt at a health care solution for a limited set of conditions is described in U.S. Pat. No. 4,712,562. A patient's blood pressure and heart rate are measured and the measurements are sent via telephone to a remote central computer for storage and analysis. Status reports are generated for submission to a physician or the patient.

U.S. Pat. No. 4,531,527 describes a similar system, wherein the receiving office automatically communicates with the physician under predetermined emergency circumstances.

U.S. Pat. No. 4,838,275 discloses a device for a patient having electronics to measure multiple parameters related to a patient's health. These parameters are electronically transmitted to a central surveillance and control office where a highly trained observer interacts with the patient. The observer conducts routine diagnostic sessions except when an emergency is noted. The observer determines if a non routine therapeutic response is required, and if so facilitates such a response. Highly trained people are needed by this system along with the special measurement apparatus that are embedded in a bed or chair.

Other attempts at a health care solution are exemplified by U.S. Pat. No. 5,012,411 which describes a portable self-contained apparatus for measuring, storing and transmitting detected physiological information to a remote location over a communication system. The information is evaluated by a physician or other health professional. As before, highly trained people are necessary to utilize such an apparatus.

Several other services to provide medical or pharmaceutical advice are now available via "1-900" telephone numbers, e.g., "Doctors by Phone." These services are available 24 hours a day and 7 days a week. A group of doctors, including some specialties, is available to answer questions about health care or medical conditions for people anywhere in the United States who call the "1-900" telephone of one of the services. A group of registered pharmacists answers questions about medications for the "1-900" pharmaceutical service.

The prior art medical diagnostic systems do not adequately provide a framework for analyzing the individual patient's clinical test results and to correlate such results with a disease biochemical marker pattern specific to that individual. Furthermore, such systems do not address therapeutic and/or contraindicated treatment strategies and the interrelation effect and pattern of metabolism of certain nutrients or drugs tailored to the individual's specific needs.

The general population is more knowledgeable today about nutrition and its importance in achieving a superior quality of life than ever before, and the trend is growing. The growing interest in the field of nutrition and health care has led to health care practitioners scrambling for knowledge that was not previously considered of critical importance, nor were many practitioners formally trained in. As a result, thousands of health conscience consumers are now desperately seeking practitioners who are knowledgeable about nutritional treatment programs and in-depth nutritional diagnostics. The knowledge of how to prevent illness, maintain health, and reverse the effects of chronic disease through dietary or nutritional intervention has become instrumental in wellness and longevity.

Nutritional supplements are a topic of great public interest. Some uses of nutritional supplements have become part of conventional medicine. For example, scientists have found that the vitamin "folic acid" prevents certain birth defects, and a regimen of vitamins and zinc can slow the progression of the eye disease age-related macular degeneration. On the other hand, some supplements are considered to be complementary and alternative medicine. The patient's interest in nutritional intervention is growing and classical medical practitioners today need a tool to bridge the gap and implement nutritional treatment options.

The advent of worldwide computer networks like the Internet has allowed many classical or alternative health care providers to reach a virtually global consumer base with relatively little cost or effort. Health care providers using the Internet are also able to provide somewhat expanded services; for example newsletters, distributions of product information or advertising, or connections to other Internet sites of potential interest to their customers. Unfortunately, the majority of health care providers through the Internet, lack the facility to appreciate consumer's individualized biochemical needs, based on each persons unique biological and chemical characteristics.

What is desirable, then, is a way for an expanded universe of consumers to reach an individualized nutritional diagnostic and treatment service provider that provides preventative, diagnostic, and treatment options to consumers based on documented research and the consumer's own biochemistry.

For consumers, electronic communication makes it possible to acquire large amounts of information tailored to their specific physiological and chemical needs. The invention described herein addresses this and other needs by allowing consumers to keep pace with the available medical research on the implications of nutrition on functions and disorders.

III. SUMMARY OF THE INVENTION

In one aspect, the present invention provides an interactive network and method for generating an individualized consumer status report that indicates the consumer's personalized nutritional information on the basis of the consumer's clinical test results and medical and biochemical research data. The network of the invention links consumers and nutritional pharmacologists, who analyze consumer's clinical test results and offer individualized nutritional information to the consumer, through a central network site.

The network provides a central integration site through which nutritional pharmacologists and consumers communicate with each other. The central integration site contains a storage medium and at least two databases stored in the storage medium. The first database maintains biochemical marker data for at least one biochemical marker in the storage medium. The first database indicates a low value, a high value and a target value for the biochemical marker indicated in the consumer's clinical test results. The target value comprises a mode value, a mean value, or a weighted average value, depending on the type of the biochemical marker under investigation. The biochemical marker level set can also be determined by generating a consumer's percent status set that indicates a value for each biochemical marker present in the consumer's clinical test results.

The second database maintains nutritional data for at least one nutrient in the storage medium, the nutritional data comprising a record for association and effect of the nutrient with a particular biochemical marker.

In one embodiment, the storage media contains a third database that maintains drug records for determining interaction between drugs and biochemical markers.

In another embodiment, the consumer is a healthy individual, a symptomatic patient, or an asymptomatic patient. The nutritional information is provided for diagnosis, treatment and/or prevention of a disease or disorder, comprising, for example, and not by way of limitation, cardiovascular disease, endocrine imbalance, cognitive impairment, immune dysfunction, gastrointestinal difficulties, anxiety, chronic fatigue, MS, eating disorders, depression, epilepsy, PMS, skin disorders, neurological impairment, developmental delay, headache, convulsion and seizure, chest pain, dizziness, irregular heartbeat, fainting, shortness of breath, chest injury, cough, high blood pressure, hyperventilation, numbness, wheezing, inhalation injury, traumatic brain injury, deficiencies in lipid metabolism, hormonal imbalance, hepatic dysfunction, toxicity, tumor, hematological diseases, nitrogen retention, cellular distortion, or a combination thereof, among others.

The nutritional information may also be based on a detectable imbalance in brain, heart, kidneys, nervous system, liver, lung, or gut of the consumer.

The nutritional information comprises one or more nutrients and/or drugs that regulate the concentration of the biochemical marker indicated in the consumer's clinical test results. Nutrients include animal products or plant products comprising herbs, vitamins, minerals, small molecules, lipids, proteins, carbohydrates, electrolytes, enzymes, coenzymes, or a combination thereof.

In another embodiment, the network of the invention provides computer networks having a user access processor, such as for example, a browser, or a script engine.

In yet another embodiment, the network utilizes the Internet, an intranet, or both.

In another embodiment, the consumer's clinical test result is entered into the central integration site through systems comprising, for example, and not by way of limitation, an interactive telephone system, an automatic speech recognition system, questionnaire forms submitted via facsimile, questionnaire forms manually entered or scanned into the computer system, a computer or telephone keyboard, a pointing device, or a combination thereof.

The communication of the status report is achieved through systems comprising, for example, and not by way of limitation, a printer, e-mail, a facsimile device, a visual display, a speech playback system, telephone, or a combination thereof.

In yet another embodiment, the consumer's clinical tests comprise tests of tissues and/or bodily fluids comprising blood tests, fatty acid tests, urine tests, or plasma tests, among others. The blood test is performed by assays such as, for example, an electrolyte panel, a platelet aggregation test, an antistreptolysin O Test, an enzyme test, a sedimentation rate determination, a determination of arterial blood gases, a glucose test, a serum myoglobin test, a complete blood count (CBC), a glycohemoglobin test, a thyroid test, a cholesterol test, a total serum protein determination, a coagulation test, a plasma ammonia test, a waste product test, a C reactive protein test, or any combination thereof.

In another aspect, the invention provides an interactive computerized method of linking consumers and nutritional pharmacologists offering consumers personalized nutritional information through a central network site, the method comprising: a) providing a central integration site through which the nutritional pharmacologists and the consumers communicate with each other, the central integration site comprising a storage medium, b) storing a first database for maintaining biochemical marker data information for at least one biochemical marker in the storage medium; c) storing a second database for maintaining nutritional data for at least one nutrient in the storage medium, the nutritional data comprising a record indicating association and effects of at least one nutrient with at least one biochemical marker; d) receiving the consumer's clinical test result from the central integration site; e) generating the consumer's biochemical marker level set by comparing the consumer's clinical test result and the biochemical marker data information of the first database; f) comparing the consumer's biochemical marker level set with the nutritional data stored in the second database; g) generating a status report indicating the consumer's personalized nutritional information; and h) communicating the status report obtained in step (g) to the consumer.

In another aspect, the invention provides a method for establishing and operating an interactive computer network linking consumers and nutritional pharmacologists through a central integration site, the method comprising the steps: a) building a central integration site to which consumers and nutritional pharmacologists connect electronically to exchange nutritional information, the central integration site comprising a storage medium containing two or more databases that store medical research data on association and effects of biochemical markers and nutrients; b) establishing commercial relationships through the central integration site between the consumers and the nutritional pharmacologists; c) linking the consumers to a plurality of services and products available through a user interface to the central integration site; d) establishing means to receive the consumer's clinical test result from the central integration site; e) generating a status report indicating the consumer's personalized nutritional information; and f) establishing means to communicate the status report obtained in step (e) to the consumer.

In yet another aspect, the invention provides for a computer program product comprising a computer useable medium having program logic stored thereon, wherein the program logic comprises a plurality of machine readable codes to enable the computer network of the invention to link consumer and non-consumer members offering products, information and services through a central network site, wherein the plurality of machine readable codes enables the central network site to collect and store the offered information, enables the central network site to manage content, organization and presentation of the offered information, maintain network interfaces, recruit network members, and/or fulfill requests for the information or services offered through the central network site.

IV. BRIEF DESCRIPTION OF THE FIGURES

FIG. 7 is a flow chart illustrating the basic formulation of software of the present invention.

FIGS. 8A and 8B are graphs illustrating two methods in which high, low and normal levels of a biochemical marker are determined in conjunction with the present invention. FIG. 8A represents a symmetrical bell shaped curve. FIG. 8B represents an asymmetrical curve.

Figures 2, 9A:
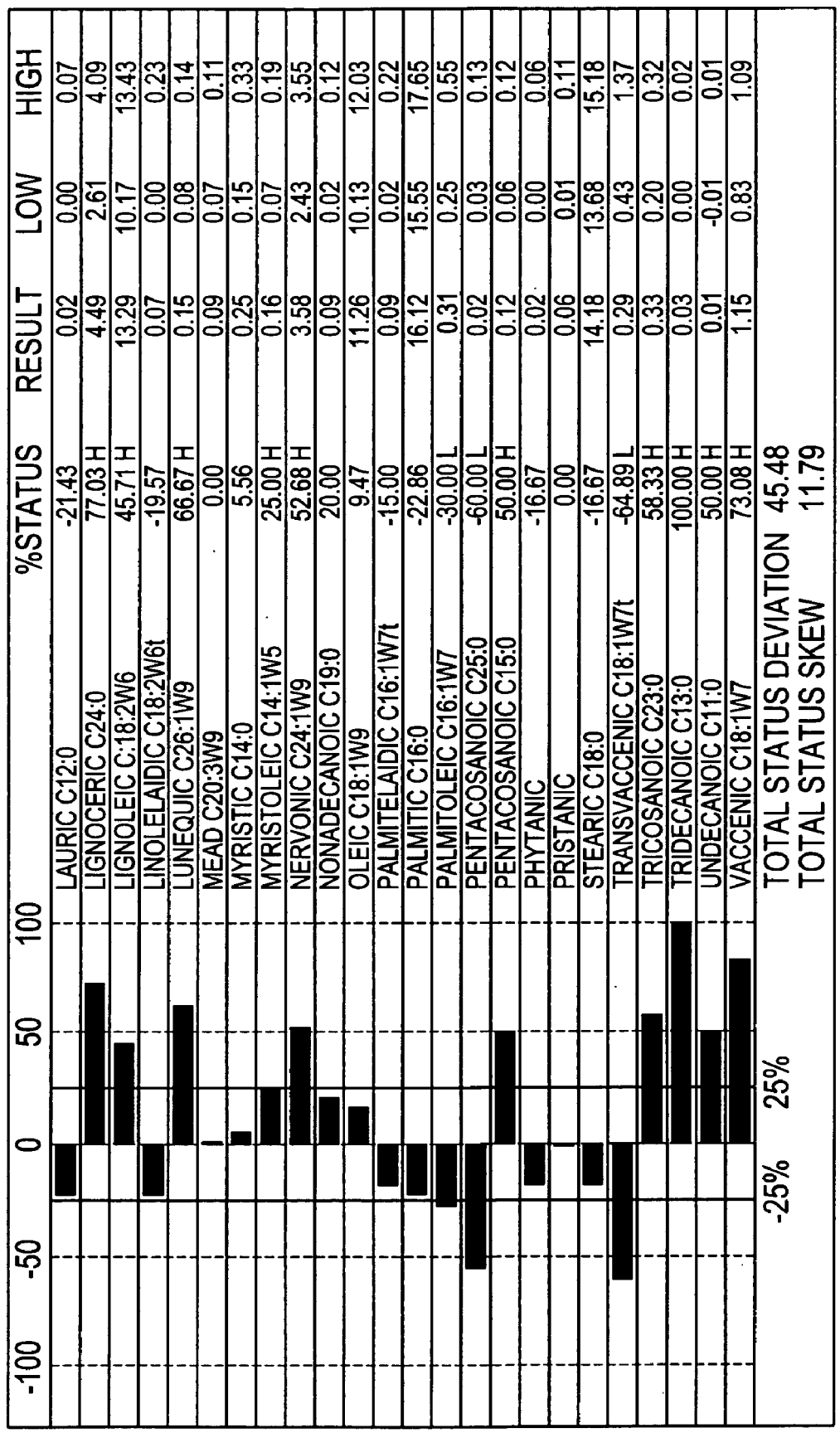
FIG. 2 is a diagram of data flow within an exemplary network.
Figures 1, 9B:
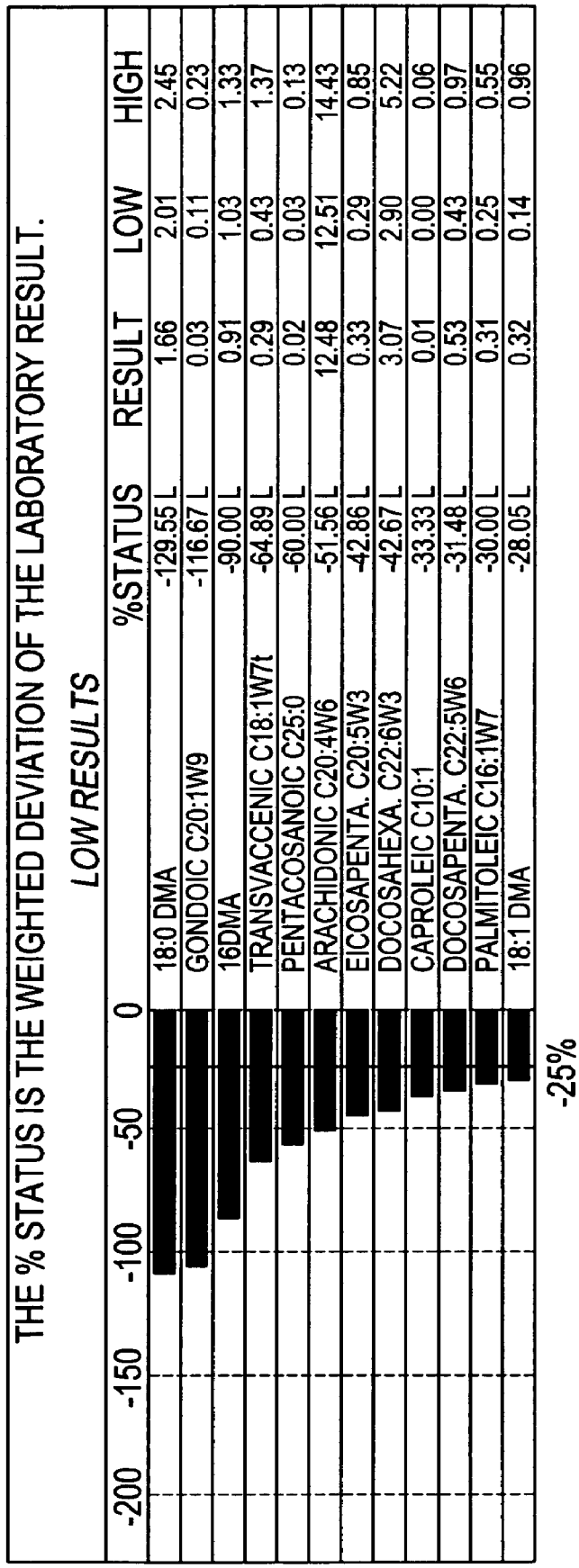
Figures 2, 9B:
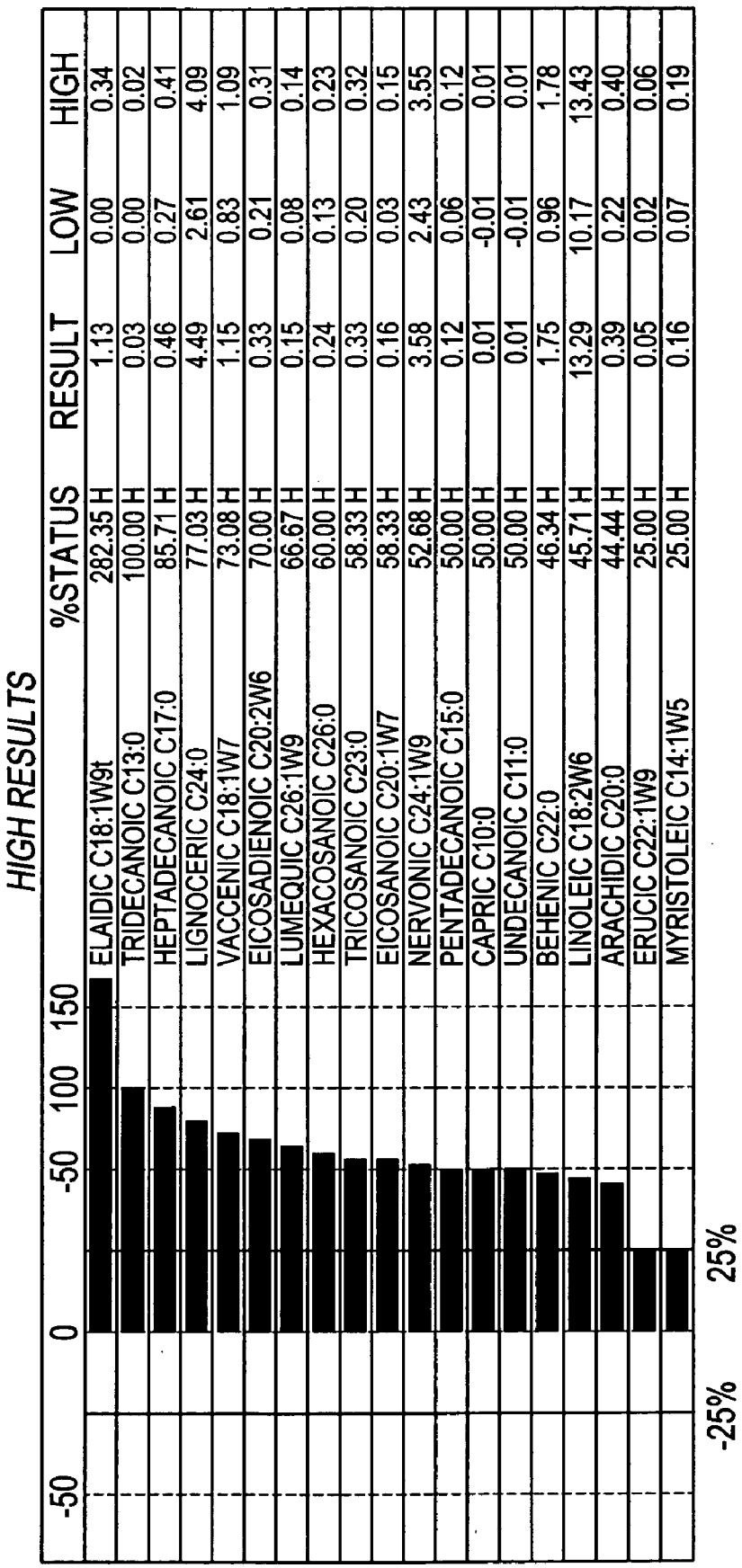
Figures 2, 9C:
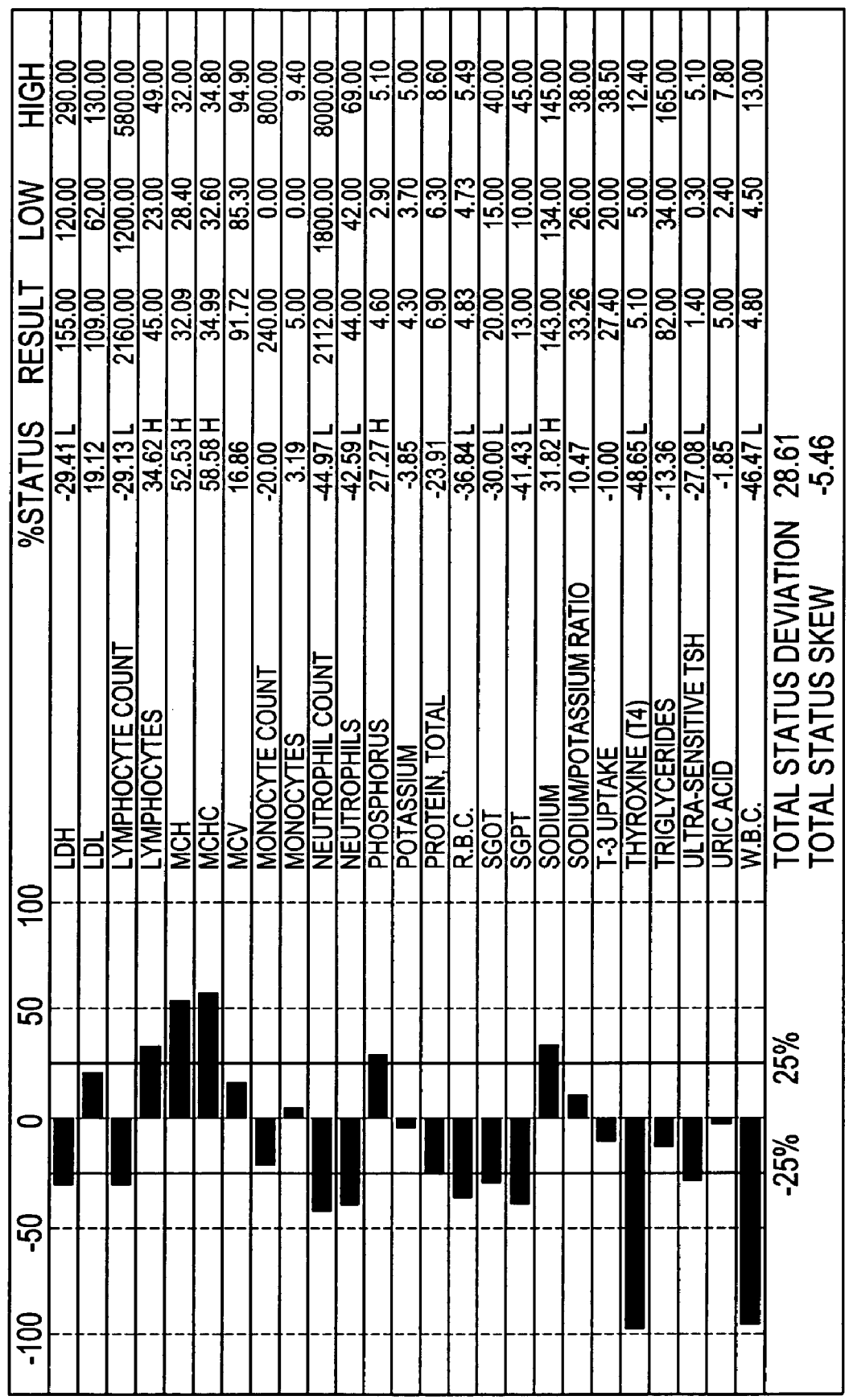
Figures 2, 9D:
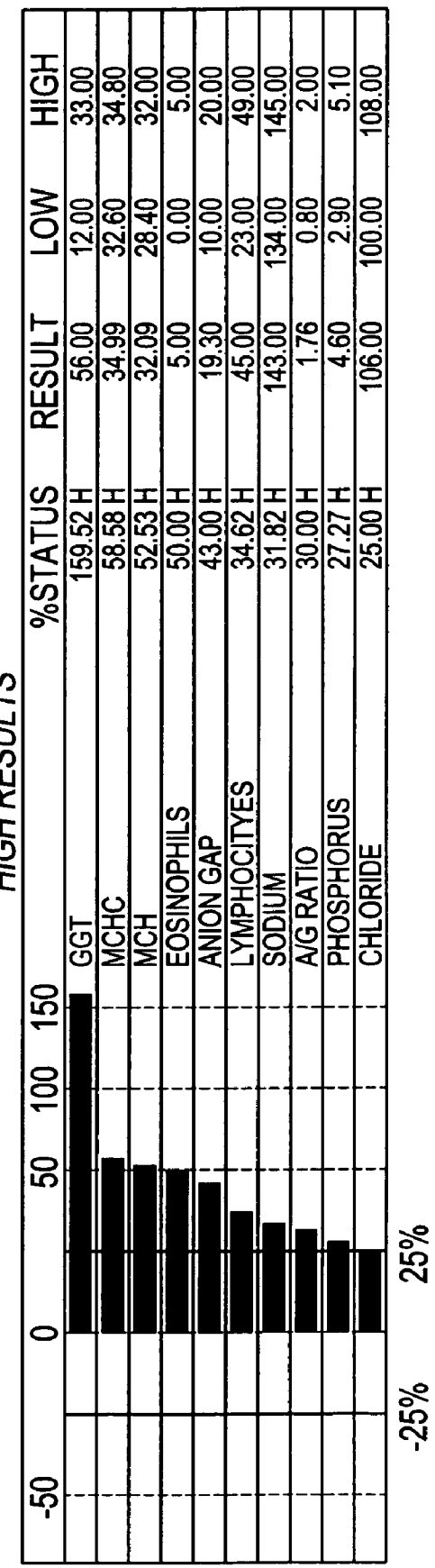

FIGS. 9A-9D are examples of basic status reports generated by the present invention. FIGS. 9A-9B provide a listing of fatty acid biochemical markers detected by a blood chemistry test. FIGS. 9C and 9D provide a listing of the non-fatty acid biochemical markers detected by the blood chemistry test. The acronym "DMA" stands for dimethylacetyl. The code following a listed fatty acid defines the number of carbon atoms in the acid and the number and location of any double bonds. For example, "Adrenic C22:4. Omega 6" denotes adrenic acid, having twenty-two carbon atoms with four double bonds, the first of which is located at the sixth carbon atom from the omega or tail end of the carbon chain.

Figure 10:
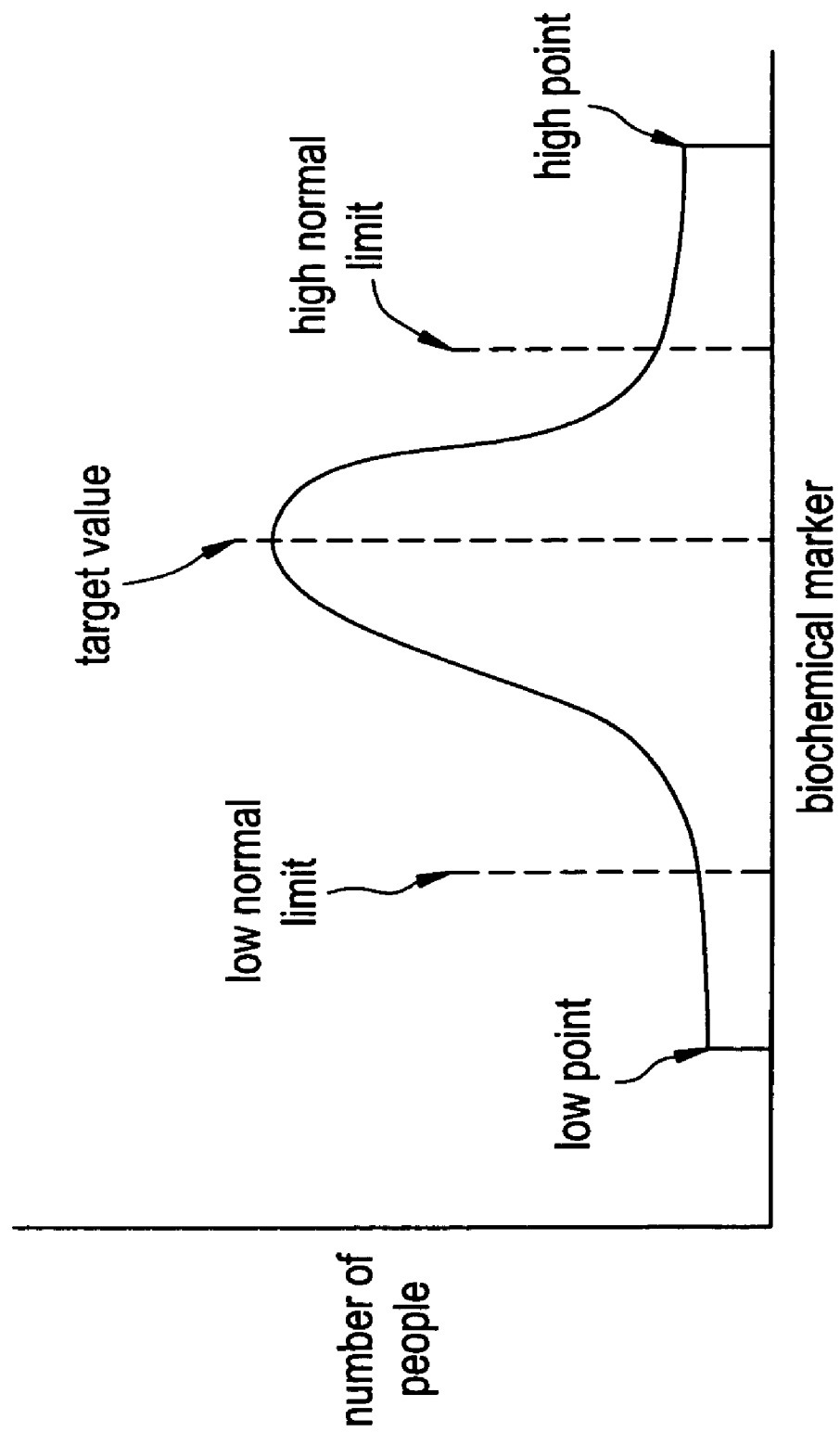

FIG. 10 is a graph illustrating another manner in which high, low and normal levels of a biochemical marker are determined in conjunction with the present invention.

Figure 11:
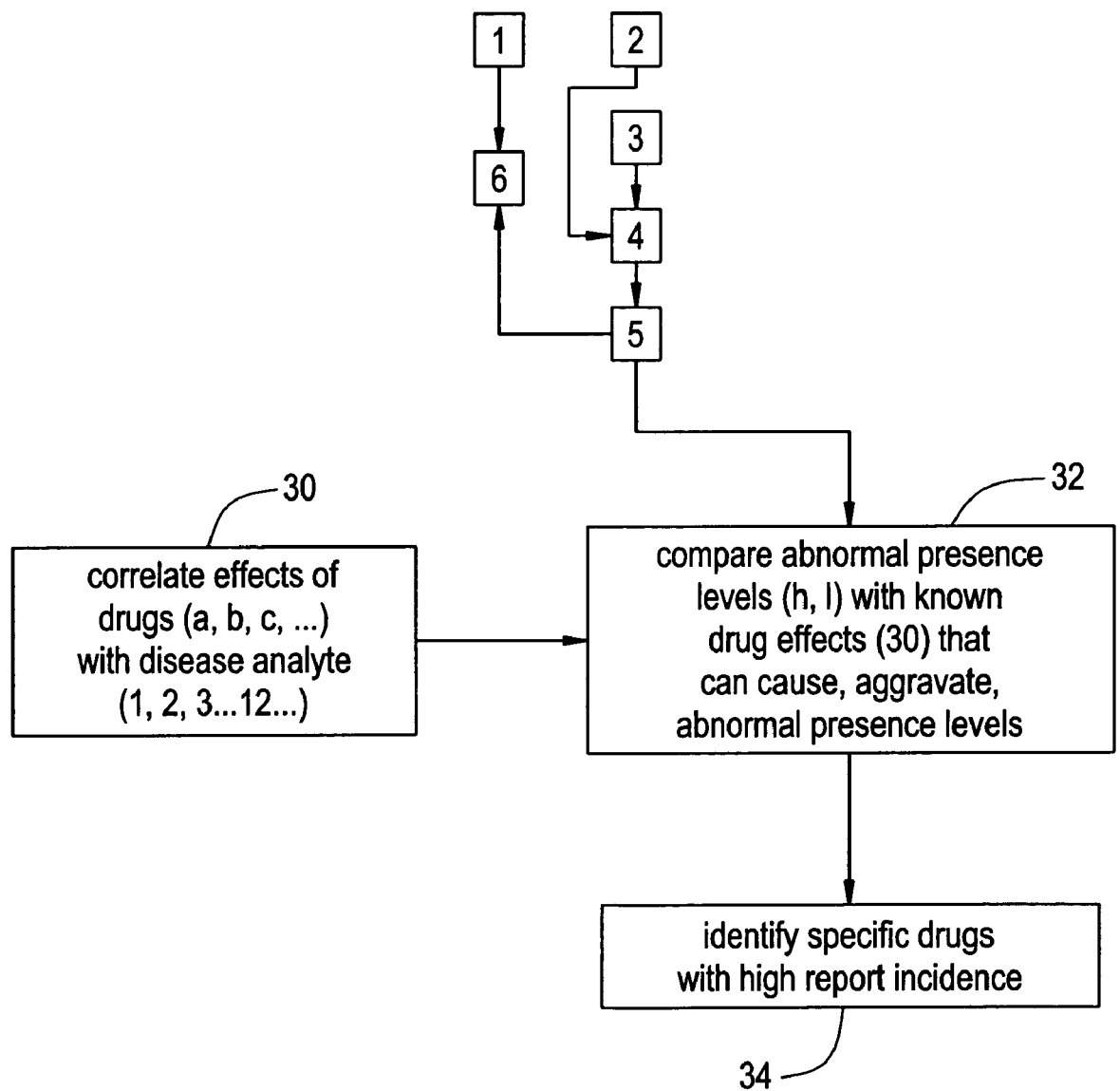

FIG. 11 is a flow chart showing the incorporation of known drug effect data with the status level of a biochemical marker, to identify drugs with high status report incidence.

FIG. 12 is a flow chart showing the utilization of known effects of nutrients on biochemical markers.

V. DETAILED DESCRIPTION OF THE INVENTION

DEFINITIONS

As used herein "biochemical markers" are molecules and/or compounds that are expressed, or formed, or otherwise present in the body and include, but not limited to, analytes, and disease indicators.

As used herein "small molecules" include, but are not limited to, carbohydrates, carbohydratemimetics, peptidomimetics, organic or inorganic compounds (i.e, including heteroorganic and organometallic compounds) having a molecular weight less than about 10,000 grams or less per mole and salts, esters, and other pharmaceutically acceptable forms of such compounds.

As used herein "network participant" means any entity, including the central integration site, which engages in the access, storage or exchange of information on the network.

As used herein, "remote member" means any network participant other than the central integration site. A remote member is either a "consumer remote member" (CRM) or a "non-consumer remote member" (NRM).

The present invention provides a network and methods for establishing and operating the network. The network of the invention links consumers, nutritional pharmacologists, and other interested parties around a central integration site (CIS). The CIS is the host of the network into which individualized information flows, stored and shared with the nutritional pharmacologists and individual consumers. The network thus facilitates the continuous collection, storage and exchange of information regarding nutritional products, drugs, biochemical markers, and provides each participant with access to an up-to-date, nutritional status reports and a wide pool of knowledge and expertise that can be manipulated to provide a variety of services.

The network of the invention provides status reports, through the use of a software to bridge the knowledge gap between applied nutritional research, classical medicine, and patients interested in nutrition as a component of their health care. In a preferred embodiment, the invention uses a software program designated "BIOCELL™" as described in U.S. Pat. Nos. 6,063,026 and 6,277,070, each of which is incorporated herein by reference in its entirety. BIOCELL™ links clinical test results to the latest medical and biochemical research from over 300 medical books and peer-reviewed scientific publications to specifically identify individualized nutrient deficiencies and imbalances, to uniquely identify drugs that would be contra-indicted for the individual, and to determine an individual's specific nutritional profile and/or drug interaction.

The network of the invention receives and analyzes the information generated from an individual's clinical test results and prepares an individualized, user-friendly status report that can be used to accurately diagnose and/or develop treatment programs and recommend dietary changes and supplement programs. Consumer's clinical test results are obtained through a variety of clinical tests, including for example, blood testing, or testing other bodily fluids and/or tissues including serum and urine test. Blood tests are performed by assays such as, for example, electrolyte panel, platelet aggregation, antistreptolysin O Test, enzyme test, sedimentation rate, arterial blood gases determination, glucose determination test, serum myoglobin test, CBC (complete blood count), glycohemoglobin test, thyroid test, cholesterol test, total serum protein measurement, coagulation test, plasma ammonia test, waste product test, C reactive protein test, fatty acid red cell membrane test, or a combination thereof.

The network of the invention can be implemented in various forms including, but not limited to, a closed intranet having restricted access and resources, or an entry-on-demand network in which the members access the CIS directly via a communications line, such as a telephone link or a wireless link. Preferably, the present invention is implemented on the Internet. On the Internet, the CIS is addressed at a particular Universal Resource Locator (URL) address. Network participants may access the CIS and enter the network by addressing their Internet browsers to the URL of the CIS.

There are two principle types of network participants: consumer remote members (CRMs) and non-consumer remote members (NRMs) "remote" meaning that they are remote from the CIS. CRMs include, for example, a healthy consumer, a symptomatic patient, an asymptomatic patient, individuals who have recently obtained a clinical test result, and individuals seeking knowledge about their personal biochemical and nutritional interaction, among others. NRMs include nutritional pharmacologists, administrators and network service providers, among others.

In one aspect of the invention, one or more sites for NRMs are designed and hosted by the CIS operator, although NRMs may take an active role in placing content on the site for a CRM to find and use. NRMs, such as nutritional pharmacologists whose advice, product recommendations or status reports are solicited by the CRMs, are accessible through a link from the CIS directly to a site provided for the NRMs. NRMs provide information to the CIS, and by extension to CRMs. CRMs can enter the network and access various consumer services or information from the CIS, visit the NRMs through the CIS, and inquire of NRMs for informational and/or transactional services.

Thus, the network of the present invention serves diverse purposes for its two major member types. For the consumer member, the network is a source of product information and related nutritional status report services. For the non-consumer member, the network is a source of consumers, a pathway to interact with the customers even when the customers are not present in a physical office, and a source of valuable information about the consumer's biochemical characteristics and health issues. Specific features of the network services provided to members of the network are presented in the detailed description below.

Figure 1:
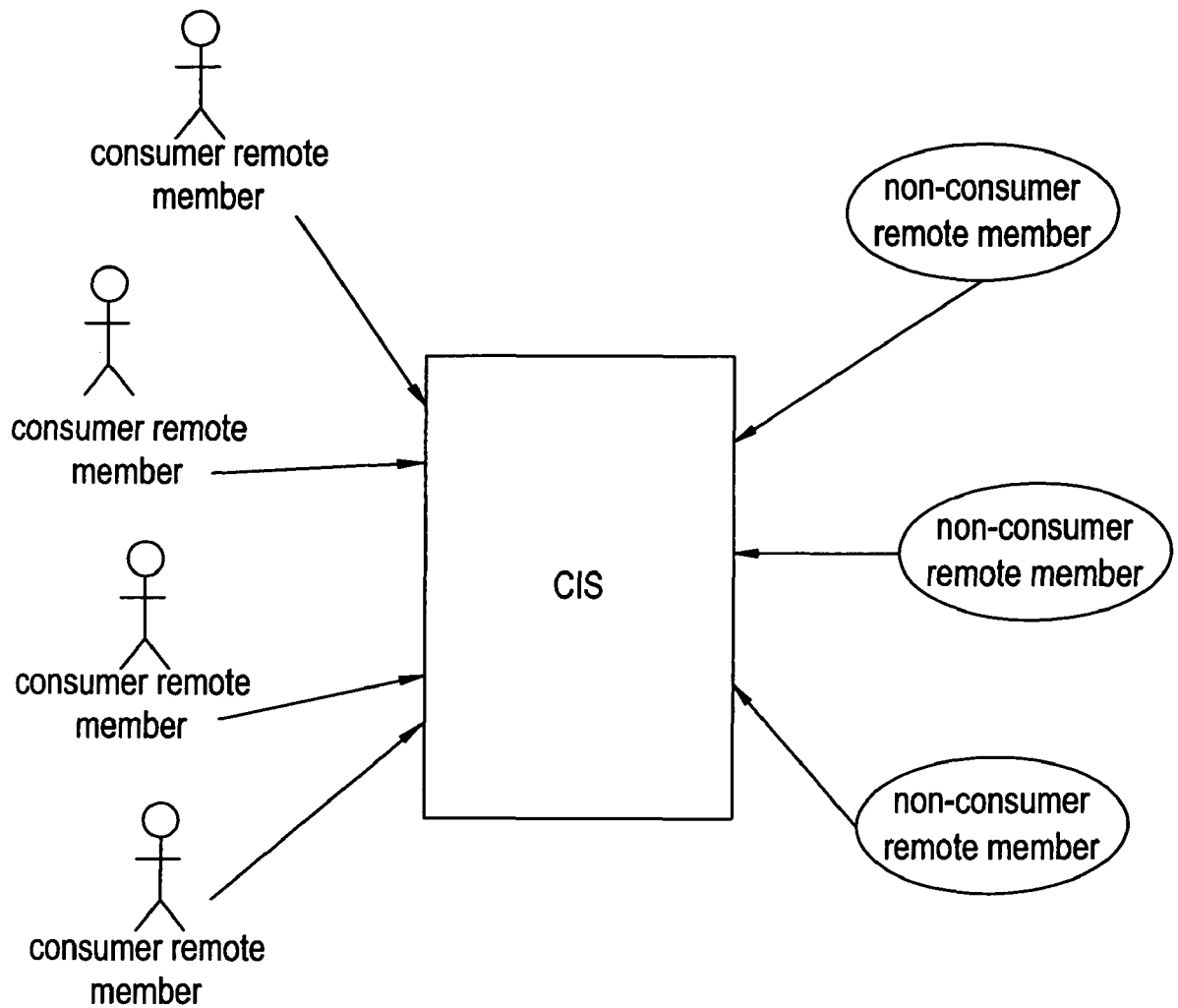
FIG. 1 shows the basic structure of an exemplary network according to the invention.

FIG. 1 shows an embodiment in which four CRMs and three NRMs are using the network. The network shown in FIG. 1 is simplified for ease of illustration, and it is understood that the networks of the present invention are in no way limited to the number of remote members shown in FIG. 1.

The CIS coordinates the collection, and subsequent exchange of information among the remote members of the network. The CIS thus comprises the operational elements (e.g., computers, central databases, service processors, central integration sites (CPUs), administrative personnel) necessary to coordinate and administer all activities of the network. The size and complexity of the CIS is directly related to the number of remote members served, or expected to be served, by the network. One of ordinary skill in the art is well aware of the operational elements required to administer a network of given complexity. Preferably, operation and maintenance of a CIS is overseen by one or more network administrators.

Networks are established by recruiting consumers, for example, by soliciting for network membership. Recruitment also includes the registering a consumer with a service provider, for example, by requesting and recording a consumer's name, e-mail address or other unique identifier and providing a new consumer account application. Typically, network membership is conditioned upon the submission of information to the network. For consumer network participants, this condition may be fulfilled by providing a unique identifier upon registration. The network sponsors (typically those who administer the network) may offer incentives or consideration for network membership over and above the benefits of network participation. For example, a consumer may be offered money and/or services (such as the free creation and maintenance of a network interface) as inducement to join the network. Once the consumer account is established, the consumer may start using the network.

According to one embodiment, a consultation for a consumer in possession of a clinical test result seeking nutritional pharmacological services typically begins with a telephone call or an E-mail to a NRM. The consumer is then asked to provide the clinical test results. The NRM may additionally ask the consumer specific questions related to the consumer's general health, genetic background, physiological and/or biochemical characteristics. Voice recognition and interactive voice response technology allow consumers to respond to multiple choice questions either by speaking directly into the telephone or by using the touch tone pad of their telephone, or key pad of their computers.

Easy access to the information in the network is also made possible by a natural user interface. An interface can be any system or device which allows interaction and information exchange between a remote member and the CIS. For example, domestic and international mail, telephone, telecopier, facsimile, and private and public computerized electronic networks. Preferred interfaces comprise private and public computerized electronic networks, such as, for example, the Internet, the wireless web, open networks where the user simply dials in, and dedicated intranets comprising remote users and a central server/data repository. A convenient and most preferred interface is the Internet.

FIG. 2 shows the data flow in an exemplary network comprising a CIS, one CRM and two NRMs. The network shown in FIG. 2 is simplified for ease of illustration, and it is understood that data flow in more complex networks is analogous to the data flow depicted in FIG. 2. To access the network, remote members interact and exchange information with the CIS through an interface.

In one embodiment, a consumer is provided with a computer-driven dialogue that consists of simple yes/no and multiple choice questions. The questions are very simply worded yet skillfully designed to obtain clinically important information from the consumer. The NRM collects information about the consumer's clinical test results and stores the information through the CIS. This information can be updated from time to time by the consumer. The CIS thus becomes an information repository that may become a source database for preparation and dissemination of individualized nutritional information and status reports to the consumer.

Access to the network preferably occurs through a central network website. The central network website allows access to network remote members, either through links to remote member web pages, or by allowing direct communication between remote members (for example, by e-mail). It is understood that the networks of the present invention can be accessed by means other than the Internet. For ease of illustration, however, embodiments of the invention will be hereinafter described as being accessible via the Internet.

Referring to FIG. 2, the CRM accesses the network via a CRM interface, for example by typing in the uniform resource locator (URL) for the central network website maintained by the CIS. Typically, network accesses by a CRM are discreet operations, that is, the CRM accesses the network for finite defined periods of time. CRMs generally will not maintain a permanent connection to the network.

Upon access to the network by a CRM, the network displays certain information, for example, general product information related to health care and nutrition, product reviews and recommendations, lists of available services, or any other information chosen by the network administrator for display. Because this information is presented to the CRM upon network access without being specifically requested, this information is termed "unsolicited information." The unsolicited information is derived from the central database of the CIS, which is a repository of all information possessed by the network, including information provided and/or collected by remote members.

In addition to reviewing the unsolicited information, the CRM can also request a network service. Network service requests are input through the CRM interface, and are submitted to the network service processor. The service processor categorizes the request and executes the appropriate service procedure. The end-result of an executed service is called "service output." Network services may comprise both informational and transactional services. If the requested service is informational (e.g., request to locate a certain product or request to view a database), the service processor accesses the CIS central database for the desired information and forwards the information through the service output to the CRM. If the requested service is transactional (e.g., request for a status report on the basis of the consumer's personal clinical test results) the service processor performs the necessary actions to effect the desired transaction and displays the result or informs the CRM that the transaction has been completed.

In further reference to FIG. 2, the NRM collects information relating to a consumer's clinical test results, or general nutritional information request through the network. The NRM accesses the network through a non-consumer remote interface, for example by connecting to the central network website via the Internet, and inputs this information to the CIS central database. The CIS organizes and stores this information in the central database. Information submission by the NRM can be on a regular basis (e.g., regular submission of a consumer's individualized status report at defined intervals).

Figure 3:
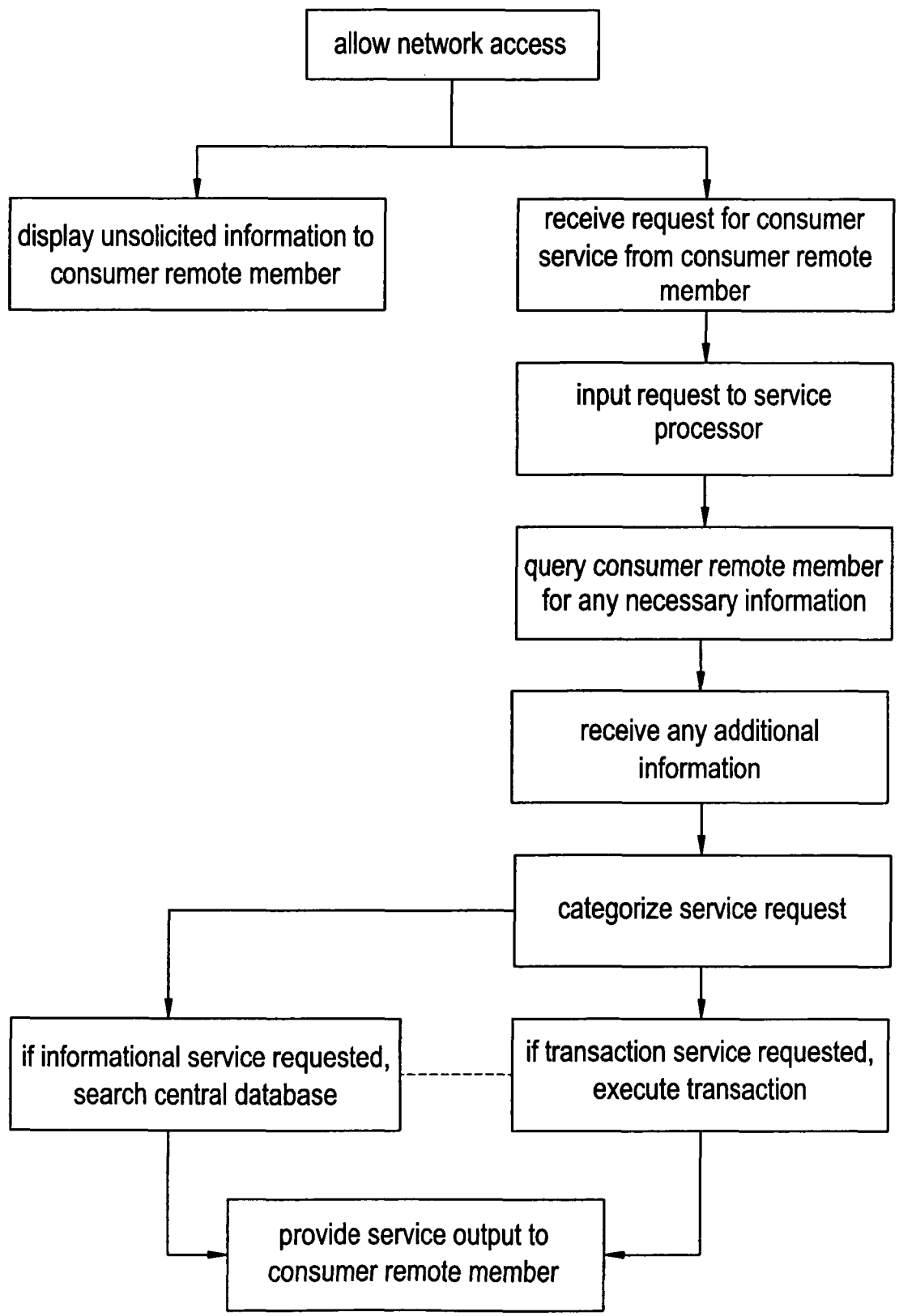
FIG. 3 is a flow chart of network operation when accessed by a consumer remote member.

FIG. 3 shows a flow chart of network operation by a CRM. Referring to the figure, the network allows access by a CRM. The network then displays unsolicited information to the CRM. The CRM may either view the unsolicited information and end the network session, or request a consumer service from the network. If a consumer service is requested, the network queries the CRM for any additional information necessary to process the request. The service processor then receives any additional information input from the CRM and categorizes the request into an informational service or a transactional service. If an informational service is requested, the service processor searches central database and/or queries other remote members for the desired information. For example, if the consumer asks the network to locate a product, the service processor will query the CRM for product specifics (e.g., product name, catalog number, or the like). If a transactional service is requested, the service processor executes the desired transaction. The service processor then provides the service output to the CRM. The CRM may then terminate the network session or request another service.

Information may flow from the CIS to the NRM upon request of the NRM. As used herein, a "request" for information by the NRM includes both discreet requests and standing requests for automatic updates. For example, a discreet request may consist of a query for an update on the metabolic pharmacology of certain biochemical markers, product availability for the purpose of enhancing inventory or obtaining a special item. An example of a standing request for an automatic update is a request that the CIS periodically send NRMs clinical test results, and scientific updates on certain drug/drug or drug/food interactions. Such requests and returns are analogous to the informational and transactional services provided to CRMs via the service processor.

Figure 4:
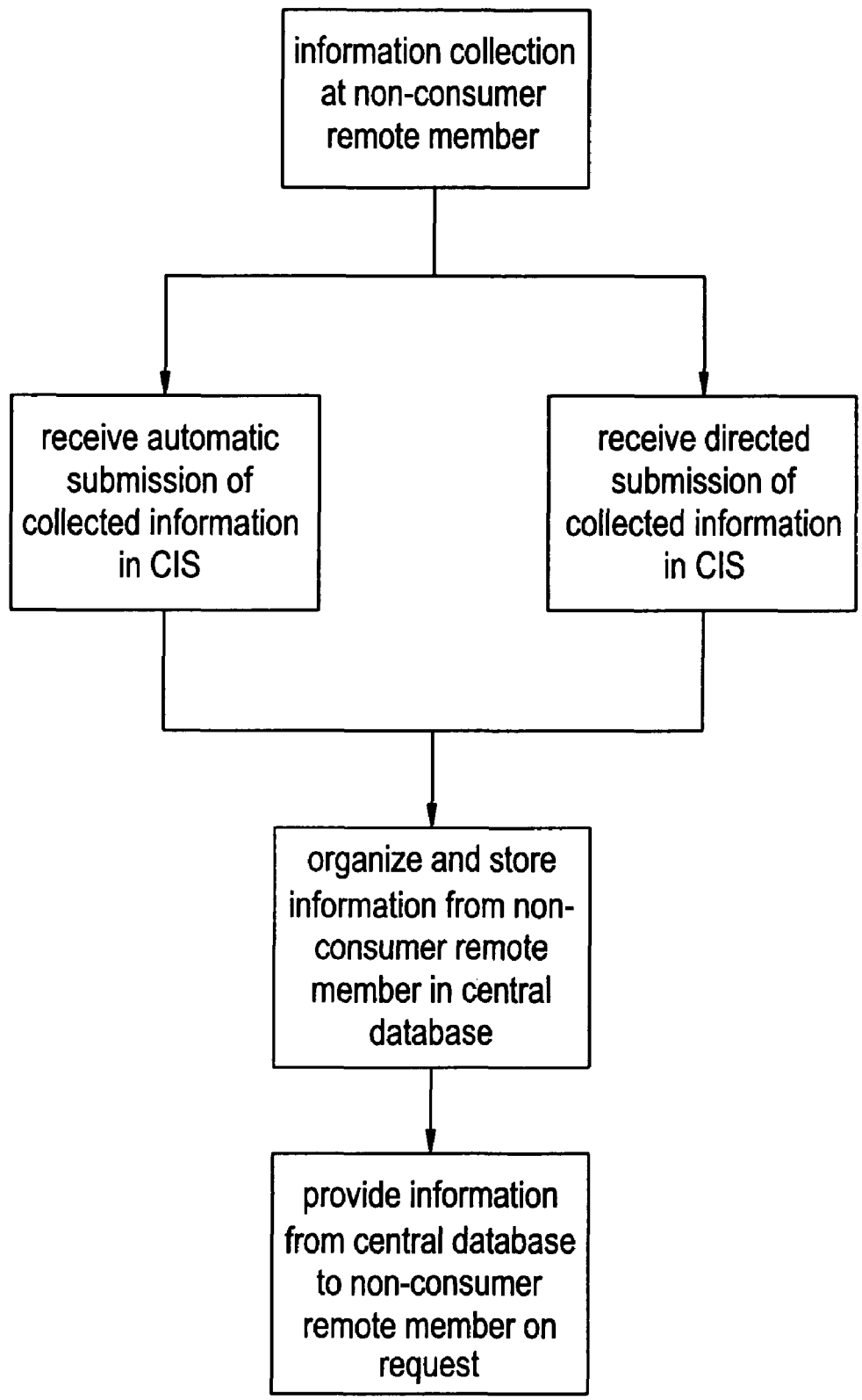
FIG. 4 is a flow chart of network operation when accessed by a non-consumer remote member.

FIG. 4 shows a flow chart of the network operation by a NRM. Information is collected at the NRM. The information relates to, for example, medical research updates on certain biochemical markers, nutrients, and/or drugs, for updating one or more databases. The CIS then receives the information by either automatic or direct submission. The CIS organizes and stores the information submitted by the NRM in the central database. The CIS provides information from the central database to the NRM upon request.

The development of on-line computerized electronic networks greatly facilitates the construction, maintenance and operation of the present networks. However, it is understood that the present networks and methods are not limited to computerized electronic networks. Networks of the present invention can be created and maintained through any system of information exchange and storage.

Figure 5:
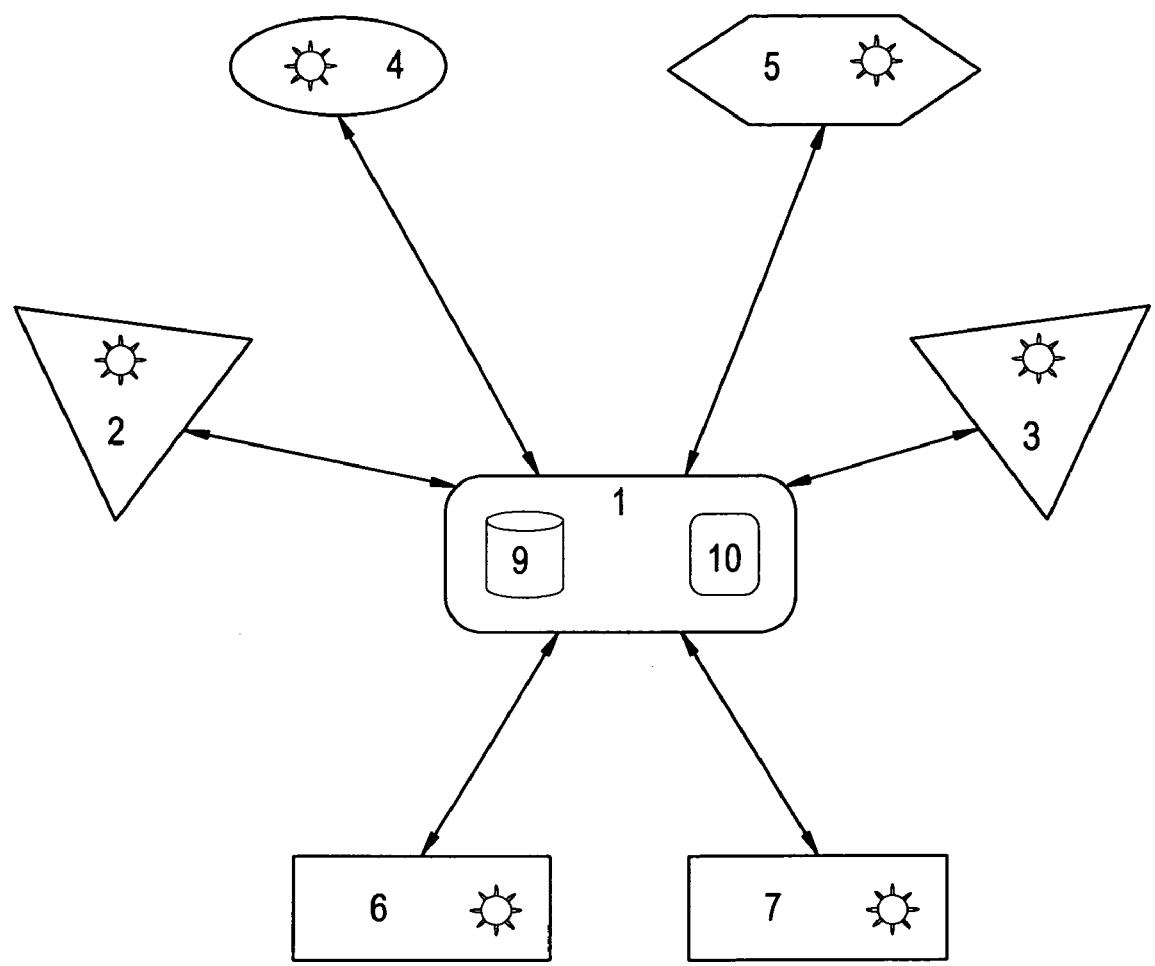
FIG. 5 is a schematic of an exemplary network.

An exemplary network is shown in FIG. 5. It is understood, however, that the present networks are not limited to the number of remote members or structure of the network in FIG. 5. With reference to FIG. 5, the network comprises a central integration site (CIS) 1 connected to remote consumer members 2, 3, 4, and 5 which are separate consumers in physically different locations and remote member non-consumer members 6, and 7. The CIS 1 comprises an information storage media 9 for storing databases and storing information received from the network members by the CIS. Any system for the storage of information can be used. Useful information storage media include, for example, printed or written matter and computer readable media. Computer readable media include, for example, paper storage media (e.g., punch cards, punch tape and the like), magnetic storage media (e.g., computer disc including "floppy" discs or diskettes, magnetic tape and the like) and light-based electronic storage media (e.g., compact disc, digital video disc, and the like). The CIS can employ one or more information storage media which can be of the same or different type. Preferred information storage media comprise computer readable media.

The information storage media or information repositories contain discrete types of information that can be organized in any manner deemed useful by NRMs. The organization and content of the storage media can also be changed at any time based on the needs of the network or network participants. The Information storage media 9 preferably contains two or more databases. In one embodiment, the information storage media contains two databases. The first database stores biochemical marker data information for a plurality of biochemical markers in the storage medium. Each item of biochemical marker data includes a biochemical marker low value, high value, and a target value. The target value includes a mode value, mean value, and a weighted average value. These values are obtained through statistical analysis of biochemical markers values obtained from testing a human test group.

The second database stores nutrient information for a plurality of nutrients in the storage medium. Each nutrient record includes a set of biochemical markers associated with the particular nutrient and the effect that the particular nutrient has on the associated biochemical marker.

In the embodiment shown in FIG. 5, CIS 1 further comprises service processor 10 to provide consumer services to CRMs. A service processor comprises any operational element by which the network can provide a requested service, including administrative personnel, printed indices or catalogs and electronic communications devices such as telephones or faxes, and computers. Preferred service processors comprise a computer with a central integration site and computer program product comprising a computer useable medium having program logic stored thereon, wherein the program logic enables the computer to perform a desired consumer service. The consumer services provided are related to the information collected by the network.

The remote members 2, 3, 4, 5, 6, and 7 each comprise collecting means 11 for collecting information from the remote members. The collecting means typically resides with the remote member and comprises means that can be used to collect and store information, for example a written instrument such as a questionnaire, a device that tracks, tabulates and/or manipulates data, an electronic device that records information, e.g., a magnetic or light-based media recorder, a scanner (including magnetic scanners as for a credit card or customer account card, and light-based scanners for reading product codes), an optical character reader, a computer, or a point-of-sale system, or a combination thereof. A remote member can employ one or more collecting means, which means can be of the same or different types.

The network further comprises exchange means 12 through which remote members interact with the network and exchange information with the CIS. As described above, the interface comprises any means for interacting with the CIS, but preferably comprises a computerized electronic network such as the Internet.

In one aspect, the invention provides a method for the creation and maintenance of CRM personal databases, in which CRM personal information is collected by a remote member and stored for subsequent access by the CRM, NRMs or both. The information in a CRM personal database can be stored by the remote member, by the CIS, or both. Personal consumer databases may include past and/or present medical history, clinical test results, and/or status reports, among others. The network protects and secures all databases of the invention, and in particular personal consumer's databases against unauthorized access.

The network of the invention provides variety of services including, for example, administrative services, receiving consumer's clinical data, generating consumer's individualized status report, creation and maintenance of CRM personal databases, requesting specific product or information, periodic exchange of information relating to remote members, e.g., consumer's clinical information, interaction between the consumer and nutritional pharmacologists, interaction between the consumer and other employees and management of NRMs including administrators of the network, and with other consumers. Such interaction can include, for example, the creation or maintenance of consumer groups (e.g., general interest groups, product use groups and product test groups), message posting services (e.g., "chat rooms" or bulletin boards), and direct consumer-to-consumer communication (e.g., e-mail).

Additionally, the network of the invention provides services related to remote purchase and/or sale of nutritional products including, ELYTE LIQUID MINERAL™, ELYT BALANCED ELECTROLYTES™, ELYTE SPORT™, DETOXX BOX™, BODY BIO BALANCE™, among others. Product recommendations also include recommendations for purchasing similar or related products based on the consumer's medical history, clinical test results, and stated taste or smell likes/dislikes.

Administrative functions of the network include, for example, collecting and storing network information, managing the content, organization and presentation of information on the network, maintaining network interfaces, recruiting network members and fulfilling requests for information or network services. Administrative functions can be performed by the CIS, NRMs and/or CRMs.

Figure 6:
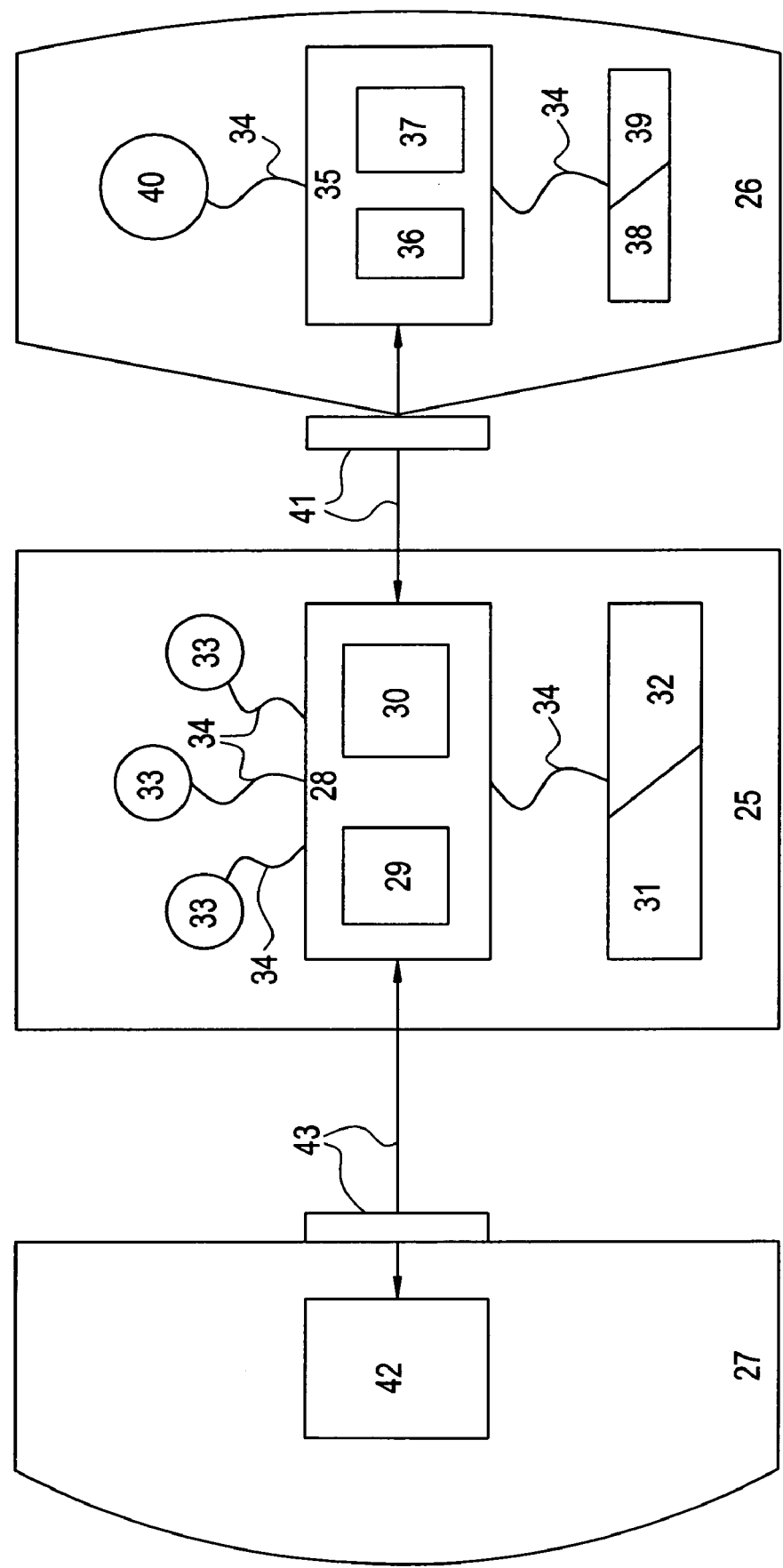
FIG. 6 is a flow chart illustrating components and topography of an exemplary computerized electronic network.

The components and topology useful in the computerized electronic networks of the invention are illustrated in FIG. 6. It is understood, however, that computerized electronic networks of the present invention are not necessarily limited to the topology and components discussed below.

With reference to FIG. 6, the computerized electronic network comprises a central integration site (CIS) 25 connected to remote member 26 which is a nutritional pharmacologist, and remote member 27, which is an individual consumer.

CIS 25 comprises at least one computer 28 including at least a central integration site (CIS) 29 and at least one storage medium 30. The storage medium 30 may be, for example, a hard disk drive or a high density storage drive with storage media, such as a ZIP drive. Larger systems will use high volume, fast access storage devices. Computer 28 also includes at least one input device 31, (e.g., keyboard, mouse, devices for receiving electromagnetic energy such as an antenna or dish, fax/modem, or disk drive) and at least one output device 32, such as a monitor, printer or disk drive. Input device 31 and output device 32 can comprise the same device. Computer 28 acts as the network server for coordinating the input, storage and exchange of information from computers and other electronic devices located with the remote network members. Computer 28 may be connected to peripheral devices 33, such as printers, scanners or such other devices as are necessary for administering the network. CIS 25 further comprises at least two and preferably three or more databases stored on storage medium 30, which databases include information from remote members 26 and 27, biochemical marker database, nutrient database, and drug/drug interaction database, among others.

The computers and other electronic components of CIS 25 are preferably internally connected by data transfer media 34, for example cable media (e.g., wire or fiber-optic cable) or wireless media, for example devices that transmit and receive electro-magnetic energy (e.g., infrared light, radio frequency, or microwave transmitters/receivers).

Remote member 26 (the nutritional pharmacologist) employs at least one computer 35 including at least a central integration site (CIS) 36 and at least one storage medium 37. The storage medium 37 may be, for example, a hard disk or a high density storage drive with storage media, such as a ZIP drive. Computer 35 also includes at least one input device 38, (e.g., keyboard, mouse, devices for receiving electromagnetic energy such as an antenna or dish, fax/modem, or disk drive) and at least one output device 39, for example a monitor, printer or disk drive. Input device 38 and output device 39 can comprise the same device. Remote member 26 further employs a data collecting device 40, which is an electronic device that records information, e.g., a magnetic or light-based media recorder, a scanner (including magnetic strip scanners as for a credit card or customer account card, and light-based scanners for reading product codes), an optical character reader, a computer, or a point-of-sale (POS) system. Computer 35 can be integral with data collection device 40, especially where it comprises a POS system.

Typical POS systems may include the following components: computers, cash registers/cash drawers, bar code readers/scanners, magnetic card or strip readers, pole displays, receipt printers, electronic scales, modems, keyboards (including keyboards with integrated magnetic strip/card readers and barcode scanner ports), and hand held data collectors (e.g., number pads for inputting credit or debit card personal identification numbers), among others. A POS system may also be modified to enable exchange information with the network. One of ordinary skill in the art is capable of modifying a POS system to exchange information with the network.

Typical POS systems can perform multiple levels of information collection, tracking and storage based on the information directly input by the remote member and information generated through customer purchases. The information collected by the POS system is input to the network, preferably by exchange with the network CIS and it is shared with the network either by direct submission or automatic exchange by remote member 26 with CIS 25. Other information can be input to the network by the remote member 26 through the POS system or other collecting means.

Remote member 26 further employs interface 41 which allows remote member 26 to interact with CIS 25 and perceive network information. Interface 41 preferably comprises an Internet connection which allows access to the CIS.

Remote member 27 (the individual consumer) employs data collection device 42, which is an electronic device that records information, e.g., an optical character reader or a computer. It is preferred that data collection device 42 comprises a computer. For example, data collection device 42 can comprise an individual consumer's home computer through which the consumer inputs information to the network.

Remote member 27 further employs interface 43 which allows remote member 27 to interact with CIS 25 and perceive network information. Interface 43 preferably comprises an Internet connection through which remote member 27 can access the central network website maintained by the CIS. Interface 43 may be located with remote member 27 (e.g., the consumer's home computer) or may be located elsewhere and be accessible to remote member 27. Interface 43 may also be located within remote member 26 (nutritional pharmacologist), and may be the same or different as interface 41. For example, remote member 26 may have an in-store, stand-alone interface for customers to access the network. Such a stand-alone interface can comprise a computer. Preferably, an in-store stand-alone interface comprises a defined area (e.g., a laboratory, or office) containing at least one computer configured for network access.

FIG. 7 is a flow chart setting forth the various steps in the formation and use of the software of the invention in the nutritional diagnostic and and/or prevention programs. In step 101, a first database is created and stored in a storage medium. The first database maintains data for a plurality of biochemical markers determined from a statistical analysis of the biochemical marker values obtained through testing a human test group. Each of the subjects of the test group is screened for a particular set of biochemical markers. For example, each subject is screened for a set of fatty acid biochemical markers and a set of non-fatty acid biochemical markers. A value representative of the amount of each of the fatty acid biochemical markers and the non-fatty acid biochemical markers is determined and becomes part of the statistical analysis. The fatty acid biochemical marker values may be obtained by drawing a blood sample from each subject and conducting a conventional fatty acid red cell membrane test known to those skilled in the art. The non-fatty acid biochemical marker values may be obtained by drawing another blood sample from each subject and conducting a conventional blood chemistry test known to those skilled in the art on the sample.

Table 1 is representative of the first database.

TABLE 1

| BIOCHEMICAL MARKER | LOW VALUE | HIGH VALUE | MODE VALUE |
|---|---|---|---|
| 1 | 25 | 150 | 90 |
| 2 | 5 | 26 | 14 |
| 3 | 8.5 | 10.8 | 9.6 |
| 4 | 96 | 109 | 103 |
| 5 | 1.9 | 3.5 | 2.6 |
| 6 | 3.90 | 9.0 | 4.7 |
| 7 | 0 | 240 | 170 |
| 8 | 3.3 | 4.5 | 3.5 |
| 9 | 140 | 260 | 190 |

In a preferred embodiment, the first database includes a low value, a high value and a biochemical marker target value for each biochemical marker. Biochemical markers have different types of curves representing their target values. A "biochemical marker target value" is a value on a frequency distribution curve, which is considered the healthiest value for a consumer and therefore represents the value an individual's biochemical marker levels should be driven towards.

Referring to FIG. 7, in step 102 a second database is created and stored in the storage medium. The second database maintains data information regarding a plurality of nutrients. Table 2 is representative of the second database.

TABLE 2

| LOW | NORMAL | HIGH |
|---|---|---|
| Abalone | | |
| Cholesterol | Cholesterol | Eosinophils |
| $CO_2$ | $CO_2$ | |
| GGT | Eosinophils | |
| Potassium | GGT | |
| Sodium | Potassium | |
| | Sodium | |
| Acetic Acid | | |
| | Calcium | Calcium |
| | | Sodium |
| Acetyl Carnitine | | |
| W.B.C | | Cholesterol |
| | | Triglycerides |
| | | W.B.C. |
| Acorn Squash | | |
| Calcium | Calcium | |
| GGT | GGT | |
| Adenosylcobalamin | | |
| Phytanic | | Lignoceric C24:0 |
| Pristanic | | Phytanic |
| Advera | | |
| Uric Acid | B.U.N | Protein, Total |

Nutrients are underlined and bolded.

The second database includes a nutrient record for each of the plurality of nutrients. Each particular nutrient record also includes a set of biochemical markers upon which the particular nutrient has a supportive effect. By supportive effect, it is meant that the nutrient drives a particular biochemical marker towards the normal range. Once the individual's biochemical marker level set has been generated, it can be compared to the nutrient database. This comparison provides a group of nutrients that can be prescribed to consumers to drive their biochemical marker levels towards the normal.

Table 2 is an example of a chart indicating recommended nutrients for high, low, and normal biochemical marker levels. The database includes a plurality of nutrients, for example, acetic acid. The database indicates nutrients that are associated with a biochemical marker level and hence allows determination of particular nutrients that are capable of regulating an out of normal range biochemical marker level towards the normal range. As shown, acetic acid is suggested for a high and/or a normal calcium level and a high sodium level.

The present invention also provides methods for identifying nutrients for an individual whose biochemical marker values suggest a minor imbalance. By minor imbalance it is meant that the percent status values fall between 12.5 and 25 or between −12.5 and −25. To this end, the percent status values may be input to the CIS and compared to the nutrient database to determine the nutrients that would drive the individual's biochemical marker values towards the normal value. The percent status value is indicative of a relationship between the individual's biochemical marker values and the test group's biochemical marker values. The calculation of the percent status value is described in more detail below.

Table 3 presents a typical tabulation of some known biochemical markers indicated in a consumer's clinical test results.

TABLE 3

| BIOCHEMICAL MARKER | RESULT* | LOW VALUE | HIGH VALUE | TARGET VALUE | % STATUS | PRESENCE LEVEL |
|---|---|---|---|---|---|---|
| 1. Alkaline Phosphatase | 68 | 25 | 150 | 90 | −17 | N |
| 2. B.U.N. | 9 | 5 | 26 | 14 | −21 | N |
| 3. Calcium | 9.3 | 8.5 | 10.8 | 9.6 | −14 | N |
| 4. Chloride | 108 | 96 | 109 | 103 | 42 | H |
| 5. Globulin | 2.0 | 1.9 | 3.5 | 2.6 | −43 | L |
| 6. Uric Acid | 6.0 | 3.9 | 9.0 | 4.7 | 15 | N |
| 7. Lactate Dehydrodenase | 222 | 0 | 240 | 170 | 37 | H |
| 8. Phosphorus | 3.3 | 2.5 | 4.5 | 3.5 | −10 | N |
| 9. Cholesterol | 160 | 140 | 260 | 190 | −30 | L |

*Indicates the patient's clinical test results.

In reference to FIG. 8A, the plot illustrated in this figure shows a statistical analysis for a particular biochemical marker, cholesterol in this example. This plot is representative of the value of the biochemical marker cholesterol obtained from the human test group. The horizontal axis indicates the cholesterol value. The vertical axis represents the number of individuals in the human test group that had a particular cholesterol value. In this example, the high value is 260 and the low value is 140. In a curve having this shape, the mode value is about 190. This value is used as the target value. The high and low values are determined as two standard deviations of the values generated from the human test group. The mode value is the value that has been recorded for the greatest number of people from the human test group.

In reference to FIG. 8B, the plot shows another example of a statistical analysis for a biochemical marker. Similar to FIG. 8A, the horizontal axis in FIG. 8B represents the biochemical marker value and the vertical axis indicates the number of individuals in the human test group that had a particular biochemical marker value. Through the generation of these plots and the development of the frequency distribution, it has been discovered that some biochemical markers present curves in which the mode is not the healthiest point. In these types of curves, the weighted average value is considered the healthiest point and therefore used as the target value.

Referring again to FIG. 7, the particular individual's biochemical marker values are input to the CIS, in step 103. The collected data is formulated as a basic status report indicating the consumer's biochemical marker values. Examples of such basic status reports are illustrated in FIGS. 9A-9D.

FIGS. 9A-9D are examples of a basic status report generated according to the present invention. FIGS. 9A and 9B provide a listing of fatty acid biochemical markers detected by a blood test such as fatty acid red cell membrane test. FIGS. 9C and 9D provide a listing of the non-fatty acid biochemical markers detected by a blood test such as fatty acid cell membrane test. The first database maintains a biochemical marker record for each of these biochemical markers.

The network system of the invention generates a status report that indicates specific nutritional needs of the consumer. The network of the invention studies and analyses a consumer's current clinical test results, for example, blood chemistry results, against the vast body of medical knowledge stored in the databases of the invention in a detailed and informative fashion. The disease pattern matching system of the invention enables an asymptomatic consumer to seek medical assistance for prevention and/or treatment of a diseases or disorders which were not previously identified or identifiable through classical clinical blood tests.

Clinical chemists have reported that disease entities often have blood chemistry patterns, some unique, some similar in definition to others. Using the world's body of medical research data, disease patterns are isolated through the use of the % status concept, as explained in more detail below.

The metabolic pharmacology section of the status report generated by the network system of the invention indicates disturbances in the consumer's blood chemistry that may be responsive to supplementation of electrolytes, minerals, coenzymes, fatty acids, vitamins, amino acids, herbs, lipids, proteins, carbohydrates, or a combination thereof to rectify a consumer's biochemical imbalances or deficiencies.

Pharmacological/nutritional biochemistry is one of the fastest growing areas of medicine and the databases of the invention are continually updated as new medical research comes to light. The status report suggests appropriate nutrient intervention as digestive support, nutritional support, nutrients recommended, and/or nutrients to avoid. Nutrients are prioritized with a star ranging from ½ star (less needed) to 4 stars (more needed) ratings. The greater the number of stars the stronger nutritional needs.

Different forms of nutrients are also indicated in the status report. The main concept reflected in the status report is the balance of nutrients. For example, for magnesium, magnesium glycinate, magnesium carbonate, or magnesium citrate may be indicated in the status report, depending on the consumer's specific nutritional needs.

In one embodiment, the consumer is provided with a blood chemistry status report that provides the information needed to quickly and effectively determine biochemical imbalances, unique nutritional needs, drug interactions and appropriate nutrient choices for individuals. The network system of the invention uses the results from a standard blood chemistry test and generates a comprehensive blood chemistry report that is diagnostic with prescriptive nutritional intervention.

In another embodiment, the consumer is provided with a red cell fatty acid status report that provides consumers with an analysis of their fatty acid metabolism that leads to a more accurate diagnosis and positive treatment outcome. Lipids evolve into hormones, the bilipid layer of every cell in the body, prostaglandins, immune components, and myelin. There is virtually no system of the body that does not require specific fatty acid substrates and coenzymes to maintain health and repair of bodily tissues. Insight into the body's cell membrane system is possible through examination of red cell fatty acid profiling provided by the network of the invention, which analysis can be reflective of long-term insufficiencies and imbalances in fatty acid metabolism.

Through lipid research and analysis of data stored in the database, the consumer may obtain an accurate measure of disturbances in his/her fatty acid metabolism which has been previously linked to a myriad of physical and mental disorders. Exploration of fatty acid metabolism leads the clinician to a wide realm of metabolic strategies to influence the health of the patient.

The status report of the invention also illustrates the total status deviation, which is the mathematical average of all the biochemical markers, and the total status skew, which illustrates the average direction of the changes, negative or positive. When the total status deviation is over 25% it signifies that the average of all the artifacts in the test is deviated more than 25%, which is significant and warrants attention. Over 50% deviation signifies a critical situation that should be viewed with some sense of urgency.

The status report of the invention also contains a bio system analysis portion that breaks the results into subset panels of different systems in the body. Pictorial and descriptive data is given as indicated for assessment of the following: cardiovascular disease, endocrine imbalance, cognitive impairment, immune dysfunction, gastrointestinal difficulties, anxiety, chronic fatigue, MS, eating disorders, depression, epilepsy, PMS, skin disorders, neurological impairment, developmental delay, headache, convulsion and seizure, chest pain, dizziness, irregular heartbeat, fainting, shortness of breath, chest injury, cough, high blood pressure, hyperventilation, numbness, wheezing, inhalation injury, or traumatic brain injury, or a combination thereof, among other diseases.

In step 4 shown in FIG. 7, a consumer's biochemical marker level set including a biochemical marker level for each biochemical marker value in the consumer's clinical test result is generated using the information maintained in the first database.

As discussed above, the biochemical marker level set is generated by first generating a percent status set. The percent status set includes a value for each biochemical marker in the consumer's clinical test results. The percent status value is indicative of a relationship between the individual's biochemical marker values and the test group's biochemical marker values. The percent status is calculated using one of the following equations.

If the individual's biochemical marker value is greater than the biochemical marker target value, then % status equals 50 (patient clinical test result biochemical marker value-biochemical marker target value)/(biochemical marker high value-biochemical marker target value). If the individual's biochemical marker value is less than the biochemical marker target value, then % status equals 50 (patient clinical test result biochemical marker value-biochemical marker target value)/(biochemical marker target value-biochemical marker low value). Using the "% status", nutritional pharmacologists may review each subset or body system in view of a consumer's specific biochemistry.

Table 4 presents the results of calculating the percent status for each of the biochemical marker values of the patient's clinical test result presented in Table 3. The percent status results are also presented in Table 3 for easy comparison with the other parameters.

TABLE 4

| | BIOCHEMICAL MARKER | | | | | | | | |
|---|---|---|---|---|---|---|---|---|---|
| | 1 | 2 | 3 | 4 | 5 | 6 | 7 | 8 | 9 |
| % STATUS | −17 | −21 | −14 | 42 | 43 | 15 | 37 | −10 | −30 |
| PRESENCE LEVEL | N | N | N | H | L | N | H | N | L |

"L" represents a low level presence,
"N" represents a normal level presence and
"H" represents a high level presence of the various biochemical markers.

By determining the percent status as a function of the biochemical marker target value and changing the denominator of the above referenced equations based upon the relationship of the individual's biochemical marker value and the target value, the percent status provides a very accurate and true picture of the individual's biochemical marker level relative to the healthiest value for the biochemical marker, as indicated by the target value.

The percent status as a function of a biochemical marker is used advantageously in situations where the results of the human test group do not present a symmetrical bell curve wherein the mean value and the target value are the same. If the human test group does not present a symmetrical bell curve, then the mean value will not equal the mode value. In this instance, the mean value will merely represent a mathematical average between the low value and the high value. This value will not be representative of the healthiest human value for the particular biochemical marker.

Once the percent status set is generated, the percent status result for each biochemical marker is compared to a pre-selected high status value and a pre-selected low status value. This comparison forms the basis for determining the individual's biochemical marker level for each particular biochemical marker relative to the test group.

By generating the consumer's biochemical marker level set based upon a percent status value that is a function of the target value for the particular biochemical marker, a nutritional pharmacologist will be better able to adjust the individual's biochemical marker levels towards a normal, optimal human condition.

In step 5, as illustrated in FIG. 7, the consumer's biochemical marker level set is compared to each of the nutrient records of the second database. This comparison provides the basis for determining any correlation between the individual's biochemical marker values and nutrients maintained in the second database.

In step 6, as illustrated in FIG. 7, a determination is made, based upon a comparison made at step 5 between the consumer's biochemical marker level set and each of nutrient records of the second database. The correlation between the consumer's biochemical marker level set and the nutrient records indicates whether an individual benefits from a particular nutrient. The comparison indicates a group of nutrients that have supportive effects for the individual having certain biochemical marker levels by counting the number of "pattern matches" that exist between the biochemical marker levels (L, N or H) of the consumer's biochemical marker level set and the biochemical marker levels for the various biochemical markers associated with the particular nutrient of the second database.

TABLE 5

Nutrient Indicator

| NUTRIENT | # BIOCHEMICAL MARKERS | # MATCHES | % MATCH |
|---|---|---|---|
| 1 | 5 | 0 | 0% |
| 2 | 6 | 4 | 67% |
| 3 | 5 | 2 | 40% |

Table 5 presents an example of the results of a comparison between the degree of association between a biochemical marker and a particular nutrient. The higher percent of match, the higher level of association between the biochemical marker and the nutrient. Accordingly, the method of the present invention can determine the likelihood that a nutrient will have a supportive effect on a particular biochemical marker.

In another embodiment of the present invention, generating the consumer's biochemical marker level set is accomplished by generating a normal limit set. The normal limit set comprises biochemical marker values that demarcate the boundaries for normal levels of the particular biochemical marker. The normal limit set includes a high normal limit and a low normal limit.

A frequency distribution curve obtained from the human test group is illustrated in FIG. 10. The curve includes a lower limit, labeled "low point" and an upper limit, labeled "high point." The low point and the high point are determined as two standard deviations of the results of the human test group. The method generates a normal limit value set for each of the plurality of biochemical markers maintained in the first database using the data information maintained in each record of the first database. The normal limit value set includes a high normal limit value (HNL) and a low normal limit (LNL) value.

The high normal limit value for each biochemical marker is determined using the equation: HNL=biochemical marker target value+[normal percent range (biochemical marker high value-biochemical marker target value)]. The low normal limit value for each biochemical marker is determined using the equation: LNL=biochemical marker target value−[normal percent range (biochemical marker target value-biochemical marker low value)]. The normal percent range is a constant between 0 and 1. The normal percent range is preferably between 0.25 and 0.75. The normal percent range is more preferably 0.50. For a more detailed description and analysis of % status see, U.S. Pat. Nos. 6,063,026 and 6,277,070, each of which is incorporated herein by reference in its entirety.

Therefore, the basic software system of the invention enables a nutritional pharmacologist to input an individual's biochemical marker values into a computerized system and have the system produce a listing of nutrients that will have a supportive effect on that individual's biochemical marker levels based upon the variation between the individual's biochemical marker values and the biochemical marker values of a human test group.

A further feature of the present invention is the generation of a status report indicating the known effects of various drugs on biochemical marker levels, as illustrated in FIG. 11. In one embodiment, the status report generated by the network system of the invention indicates and flags drug interactions and potential problems for the consumer taking the drug on the basis of their individual blood chemistry results. This section (usually one page) permits a quick scan to see how specific drugs affect each consumer's biochemistry differently. Through the status report generated by the network system of the invention, the consumer is able to determine which biochemical marker is affected by the drug, and ascertain whether he or she is at risk of developing a disease or disorder by taking the drug.

The drug interaction analysis of the network of the invention is made possible by the use of a third database stored on the storage media of the central integration site. The third database includes drug records that correlate the effects of known drugs upon the levels of each of the various biochemical markers.

As illustrated in FIG. 11, at step 52, the abnormal presence levels, both high (H) and low (L), of the biochemical markers are compared with the drug effects data. Drugs that negatively interact with biochemical markers are detected.

Table 6 presents known drug effect from medical research data for a few specific biochemical markers

TABLE 6

| BIOCHEMICAL MARKER | ABNORMAL PRESENCE LEVEL | DRUG NEGATIVELY AFFECT THE BIOCHEMICAL MARKER |
|---|---|---|
| Chloride | L | Acetazolamide, Aspirin, Lithium, Boric Acid |
| Total iron | L | ACTH, Oxalate, Fluorides |
| Basophils | L | Procainamide |
| WBC | L | Aspirin, Busulfan, Mepazine |
| Glucose Insulin | L | Aspirin, Ethanol, |
| Total Protein L | | Aspirin, Arginine, Rifampin |

An analysis of the data presented in Table 6 shows that the drug aspirin is identified as a drug that can negatively affect four of the six abnormal presence levels of the biochemical markers set forth therein. For example, when the level of the biochemical marker "chloride" is high (percent status is greater than 25), drugs, such as aspirin, is listed to cause or aggravate this condition. Thus aspirin is a contraindicated drug for the individual whose clinical test results are provided in Table 6.

Another feature of the network system of the invention is to provide a consumer's status report that incorporates known positive effects of various drugs on various biochemical markers. As illustrated in FIG. 12, a drug database 60 is created and stored in the storage medium. The drug database includes records that correlate the effects of known drugs that positively affect the abnormal presence level of various biochemical markers.

Thus, for each biochemical marker, known drugs are cataloged that can normalize the level of a particular biochemical marker. The effects of drugs on biochemical markers are well known in medical research. New agents and the corresponding effects thereof on various biochemical markers are developed in medical research on a daily basis. Hence, the databases used in the network system of the invention are periodically updated.

Another feature of the network system of the invention is to provide a consumer's status report that includes determining a group of nutrients that is needed based upon supportive effects of a particular nutrient on the levels of at least two biochemical markers.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. An interactive computerized method of linking a consumer and a nutritional pharmacologist offering personalized nutritional information to the consumer comprising;

providing a central integration site comprising a computer through which the nutritional pharmacologist and the consumer communicate with each other;

storing a non-transitory computer readable medium on said computer including a first database storing biochemical marker data obtained through statistical analysis of plurality of biochemical markers obtained from testing a human test group, wherein said computer determines a low, a high and a target value and a normal range of values for each said plurality of biochemical markers of said human test group; and a second database storing a nutritional record for plurality of nutrients and information on an effect of each of said plurality of nutrients has on said each of said plurality of biochemical markers obtained from said human test group;

receiving a consumer's blood test containing a numerical value for said at least one biochemical marker, wherein said at least one biochemical marker comprises cholesterol, eosinophils, potassium, sodium, phytanic, basophils, pristanic, uric acid, alkaline phosphatase, globulin, lactate dehydrogenase, phosphorous, insolin, iron, glucose, or a combination thereof;

generating a consumer's biochemical marker level set by comparing said numerical value of said at least one biochemical marker indicated in the consumer's blood test against said target value of the biochemical marker data of said first database to determine; whether the consumer's numerical value is higher than, equal to, or lower than the target value, and whether the consumer's numerical value is within the normal range of values determined for said human test group;

comparing said biochemical marker level set with said nutritional record stored in the second database to determine one or more nutrients that demonstrate a supportive effect on said at least one biochemical marker by regulating a value of said at least one biochemical marker towards said target value;

generating a status report indicating a personalized nutritional information for the consumer through said central integration site; wherein the status report shows nutrients that are indicated and/or contraindicated based on results of the comparing step;

communicating said status report to the consumer through said central integration site, and periodically updating said nutritional pharmacologist with new clinical and scientific reports regarding metabolic pharmacology of said at least one biochemical marker, wherein the method determines biochemical imbalances specific to the consumer and provides personalized treatment choices to the consumer.

2. The interactive computerized method of claim 1, wherein said one or more nutrients comprises herbs, vitamins, minerals, small molecules, lipids, proteins, carbohydrates, electrolytes, enzymes, or coenzymes, or a combination thereof.

3. The interactive computerized method of claim 1, utilizing the Internet.

4. The interactive computerized method of claim 1, utilizing an intranet.

5. The interactive computerized method of claim 1, wherein the consumer's blood test is received through systems comprising an interactive telephone system, an automatic speech recognition system, one or more questionnaire forms submitted via facsimile, one or more questionnaire forms manually entered or scanned into the computer system, a computer keyboard, a telephone keyboard, a pointing device, or any combination thereof.

6. The interactive computerized method of claim 1, wherein said central integration site communicates said status report to said consumer via a printer, e-mail, a facsimile device, a visual display, a speech playback system, telephone, or a combination thereof.

7. The interactive computerized method of claim 1, wherein the blood test comprises an assay comprising an electrolyte panel, a platelet aggregation test, an antistreptolysin O Test, an enzyme test, a sedimentation rate determination, a determination of arterial blood gases, a glucose test, a serum myoglobin test, a complete blood count, a glycohemoglobin test, a thyroid test, a cholesterol test, a total serum protein determination, a coagulation test, a plasma ammonia test, a waste product test, a C reactive protein test, or any combination thereof.

8. The interactive computerized method of claim 1, wherein said non-transitory computer readable medium further comprises a third database that maintains drug records for determining interaction between drugs and said at least one biochemical marker.

* * * * *